(12) United States Patent
Xia et al.

(10) Patent No.: US 11,097,105 B2
(45) Date of Patent: Aug. 24, 2021

(54) PULSE CURRENT GENERATION CIRCUIT FOR NEURAL STIMULATION, CHARGE COMPENSATION CIRCUIT AND METHOD, AND IMPLANTABLE ELECTRICAL RETINA STIMULATOR

(71) Applicant: SHENZHEN SIBIONICS TECHNOLOGY CO., LTD., Zhenzhen (CN)

(72) Inventors: Bin Xia, Shenzhen (CN); Yu Zhao, Shenzhen (CN); Yu Lin, Shenzhen (CN); Xianwen Fang, Shenzhen (CN); Zhi Chen, Shenzhen (CN)

(73) Assignee: SHENZHEN SIBIONICS TECHNOLOGY CO., LTD., Shenzhen (CN)

( * ) Notice: Subject to any disclaimer, the term of this patent is extended or adjusted under 35 U.S.C. 154(b) by 273 days.

(21) Appl. No.: 16/337,920

(22) PCT Filed: Sep. 29, 2017

(86) PCT No.: PCT/CN2017/104678
§ 371 (c)(1),
(2) Date: Mar. 28, 2019

(87) PCT Pub. No.: WO2017/104678
PCT Pub. Date: Mar. 28, 2019

(65) Prior Publication Data
US 2019/0224483 A1   Jul. 25, 2019

(30) Foreign Application Priority Data

Sep. 30, 2016  (CN) .......................... 201610875326.8
Sep. 30, 2016  (CN) .......................... 201610879293.4

(51) Int. Cl.
*A61N 1/36*   (2006.01)
*A61N 1/05*   (2006.01)
(Continued)

(52) U.S. Cl.
CPC ....... *A61N 1/36046* (2013.01); *A61N 1/0543* (2013.01); *A61N 1/36125* (2013.01);
(Continued)

(58) Field of Classification Search
CPC .............. A61N 1/36046; A61N 1/0543; A61N 1/36142; A61N 1/36175; A61N 1/36125;
(Continued)

(56) References Cited

U.S. PATENT DOCUMENTS

2003/0181957 A1* 9/2003 Greenberg ......... A61N 1/36046
607/54
2007/0299484 A1* 12/2007 Greenberg ......... A61N 1/36046
607/54

FOREIGN PATENT DOCUMENTS

CN   1849993 B    4/2010
CN   103170058 B  6/2015
(Continued)

OTHER PUBLICATIONS

International Preliminary Report on Patentability Chapter I.

*Primary Examiner* — Rex R Holmes
(74) *Attorney, Agent, or Firm* — Avant Law Group, LLC

(57) ABSTRACT

A pulse current generation circuit (100) for neural stimulation includes an analogue signal receiving device (101) for receiving an analogue signal; an analogue-to-digital converter (102) for converting the analogue signal into a digital control signal; a current signal controller (103) for producing, according to the digital control signal, pulse current parameters for generating bidirectional pulse current signals; and a current generator (104) for generating, according
(Continued)

to the pulse current parameters, bidirectional pulse current signals for neural stimulation, and the current generator can generate pulse currents of different precisions according to the pulse current parameters. In addition, the present invention further relates to a charge compensation circuit, a charge compensation method, and an implantable electrical retina stimulator using the pulse current generation circuit or the charge compensation circuit.

19 Claims, 8 Drawing Sheets

(51) Int. Cl.
  *H03K 3/78* (2006.01)
  *H03K 3/017* (2006.01)
  *H03K 5/00* (2006.01)
  *H03K 5/02* (2006.01)

(52) U.S. Cl.
  CPC ..... *A61N 1/36142* (2013.01); *A61N 1/36175* (2013.01); *H03K 3/017* (2013.01); *H03K 3/78* (2013.01); *H03K 5/00006* (2013.01); *H03K 5/02* (2013.01); *A61N 1/36157* (2013.01)

(58) Field of Classification Search
  CPC ...... A61N 1/36157; H03K 3/78; H03K 3/017; H03K 5/00006; H03K 5/02
  See application file for complete search history.

(56) References Cited

FOREIGN PATENT DOCUMENTS

| | | |
|---|---|---|
| CN | 103356326 B | 8/2016 |
| CN | 104689470 B | 1/2017 |

* cited by examiner

Bidirectional pulse current signal

PULSE CURRENT GENERATION CIRCUIT FOR NEURAL STIMULATION, CHARGE COMPENSATION CIRCUIT AND METHOD, AND IMPLANTABLE ELECTRICAL RETINA STIMULATOR

The present invention relates to a pulse current generation circuit, a charge compensation circuit, a charge compensation method, and an implantable electrical retina stimulator for neural stimulation.

BACKGROUND OF INVENTION

In the field of neural stimulation, nerve tissues respond to electrical stimulations from stimulation electrodes, thereby providing desired functions. For example, in the conventional vision repair system of artificial retina, in order to restore visual perception to the blind, it is generally necessary to put an implant into an eyeball of the blind. This implant functions as the photoreceptor cells that were impaired due to, for example, retinal pigmentation (RP) or age-related macular degeneration (AMD). If other functions of the visual pathway are retained, the stimulation electrodes in the implant can be used to stimulate neural pathways to restore partial vision for the blind.

In an artificial retina system, an external camera outside the body captures video images, and then an image processing device converts the video images into electrical signals and sends the electrical signals to the implant. Then, the implant in the eye converts the electrical signals into stimulation signals and stimulates ganglion cells in the retina through the stimulation electrodes of the implant, thereby enabling the blind to feel a sense of light in the cerebral cortex and restore partial vision.

SUMMARY OF INVENTION

However, in conventional artificial retinas or artificial retinal systems such as implantable electrical retinal stimulators, the stimulation signals generated by the stimulation electrode generally are capable of stimulating only nerve cells (such as ganglion cells) on the surface of the retina, and cannot effectively stimulate retinal bipolar cells slightly away from the retina surface. Therefore, the stimulation effect is seldom good. In addition, there is still much to be improved in terms of the stimulating resolution.

In addition, in the existing neural stimulation devices such as artificial retina systems, the stimulating current generated for neural stimulation may not guarantee that the charge amount during one stimulation period falls within a safe range. The nerve tissues (such as retinal ganglion cells or bipolar cells) being stimulated may therefore carry net charges, such as positive charges or negative charges, resulting in damage to the nerve tissues such as ganglion cells or bipolar cells in the retina.

To balance the stimulating charges received by the nerve tissues such as ganglion cells or bipolar cells in the retina, sometimes a RC circuit is arranged between the pulse current generation circuit and a site to be stimulated to balance redundant charges on the ganglion cells or the bipolar cells. However, charge balance performance of the RC circuit is positively correlated with the capacitance of a capacitor in the RC circuit. In order to balance more positive or negative charges, the capacitance of the capacitor in the RC circuit needs to be increased. Thus, a capacitor with a larger size is needed. However, in the field of neural stimulation, the space for the circuit is often limited, and a large capacitor occupying large area cannot be integrated into the circuit. Therefore, the RC circuit cannot fully exert its function in charge balance.

Through long-term researches, the present inventors have found that the ganglion cells are connected with multiple bipolar cells in the retina, and the bipolar cells are connected with photoreceptor cells one by one in the macular area of the retina (the place where the artificial retina is usually implanted). By stimulating the bipolar cells in the retina, the stimulating resolution can be effectively improved, thereby generating a more accurate and effective sense of light. For example, when an implantable electrical retina stimulator is arranged on the retina to restore vision of the blind, the implanted stimulation electrode is often attached to the retina so that the stimulation electrode mainly contacts with ganglion cells of the retina (especially with the axons of ganglion cells). In order to enable the stimulation signals generated by the stimulation electrode to stimulate the bipolar cells slightly away from the stimulation electrode, the stimulation electrode is generally required to provide pulse current of, for example, a wide pulse width. In addition, to provide a safe charge amount from the stimulation electrode, if the pulse width of the pulse current is wide, the amplitude of the pulse current shall be correspondingly reduced to ensure that the stimulation charges are within the safe range.

In order to solve the problems mentioned above, the purpose of the present invention is to provide a pulse current generation circuit capable of enhancing effective stimulation resolution, a charge compensation circuit, a charge compensation circuit method, and an implantable electrical retina stimulator for neural stimulation.

Thus, a first aspect of the present invention provides a pulse current generation circuit for neural stimulation, comprising an analogue signal receiving device for receiving an analogue signal; an analogue-to-digital converter for converting the analogue signal into a digital control signal; a current signal controller for producing, according to the digital control signal, pulse current parameters for generating bidirectional pulse current signals; and a current generator for generating, according to the pulse current parameters, bidirectional pulse current signals for neural stimulation, wherein the current generator can generate pulse currents of different precisions according to the pulse current parameters.

In the first aspect of the present invention, the current signal controller generates pulse current parameters for generating the bidirectional pulse current signals based on a digital control signal, and the current generator generates bidirectional pulse current signals with different precisions for neural stimulation according to the pulse current parameters. By using the current generator which can generate pulse currents of different precisions, bidirectional pulse current signals with different pulse widths and different precisions may be generated according to stimulation needs. Thus, not only the requirement of safe charge can be satisfied, but also the nerve cells (such as bipolar cells) that need to be stimulated can be effectively stimulated, thereby producing more effective stimulation effect. In another aspect, due to the pulse current generation circuit can achieve a wider pulse signal, therefore, the higher processing requirements can be adapted at a hardware level, such as stimulation algorithm optimization.

In addition, in the pulse current generation circuit according to the present invention, optionally, in one stimulation period, the total charge amount of the bidirectional pulse current signals is within the safe charge amount range. Thus, the damage of the pulse current signal to human nerve tissue (such as ganglion cells or bipolar cells in retina) can be avoided, thereby ensuring the safety and the reliability of the pulse current generation circuit.

In the pulse current generation circuit according to the present invention, optionally, the pulse current parameters include a negative pulse width, a negative pulse amplitude, a positive pulse width, a positive pulse amplitude and a pulse interval. Thus, by controlling the pulse current parameters, different stimulation pulse currents can be realized.

In addition, in the pulse current generation circuit according to the present invention, optionally, the current generator generates low-precision pulse current or high-precision pulse current according to the pulse current parameters; and the current generator determines whether bidirectional pulse current signals to be generated are less than the critical value after receiving the pulse current parameters, generates the high-precision pulse current when the bidirectional pulse current signals to be generated are less than or equal to the critical value, and generates the low-precision pulse current when the bidirectional pulse current signals to be generated are greater than the critical value. Thus, the current generator can generate the corresponding pulse currents in different situations to meet the requirement of the stimulation signal.

In addition, in the pulse current generation circuit according to the present invention, optionally, the current generator generates the high-precision pulse current when the negative pulse width of the bidirectional pulse current signals is greater than the preset duration and the negative pulse amplitude is less than or equal to the critical value. In this case, nerve cells can be stimulated more effectively.

In addition, in the pulse current generation circuit according to the present invention, optionally, the precision of the pulse amplitude of the high-precision pulse current is greater than the precision of the pulse amplitude of the low-precision pulse current. Thus, the current generator can generate the pulse currents of different precisions according to actual situations, so as to meet the requirements of different neural stimulation signals.

In addition, in the pulse current generation circuit according to the present invention, optionally, the total charge amount of the positive pulse current or the negative pulse current during one stimulation period of the bidirectional pulse current signals is within the safe charge amount range. Thus, long-term safety and reliability of the stimulation electrodes can be ensured.

In addition, a second aspect of the present invention provides a charge compensation circuit configured for conducting charge compensation on the pulse current generation circuit which is configured for generating bidirectional pulse current for neural stimulation; the charge compensation circuit includes: a detection circuit for detecting the total charge amount during one stimulation period of the bidirectional pulse current signals generated by the pulse current generation circuit; a determination circuit for determining whether the total charge amount detected by the detection circuit exceeds the safe charge amount range; and a compensation circuit for generating a compensation pulse current signal with a net charge amount when the determination circuit determines that the total charge amount exceeds the safe charge amount range, so that the total charge amount is within the safe charge amount range.

In the second aspect of the present invention, the detection circuit is configured for detecting the total charge amount during one stimulation period of the bidirectional pulse current signals generated by the pulse current generation circuit, and the determination circuit is configured for determining whether the total charge amount detected by the detection circuit exceeds the safe charge amount range. Moreover, the compensation circuit is configured for generating a compensation pulse current signal with a net charge amount when the determination circuit determines that the total charge amount exceeds the safe charge amount range, so that the total charge amount is within the safe charge amount range. In this way, the compensation pulse current signal with a net charge amount is transmitted to conduct charge balance on the bidirectional pulse current signals under the condition that a large capacitor (RC circuit) with large occupied area is not used. Thus, charge balance capability can be fully enhanced within a limited space.

In addition, in the charge compensation circuit according to the present invention, in the compensation circuit, when the determination circuit determines that the total charge amount is a positive value, a compensation pulse current signal with a negative compensation charge amount is generated so that the total charge amount is within the safe charge amount range; and when the determination circuit determines that the total charge amount is a negative value, a compensation pulse current signal with a positive compensation charge amount is generated so that the total charge amount is within the safe charge amount range. Thus, the total charge amount for neural stimulation is effectively ensured to be within the safe charge amount range.

In addition, in the charge compensation circuit according to the present invention, optionally, the amplitude of the compensation pulse current signal is lower than a preset amplitude, and the period of the compensation pulse current signal is less than the period of the bidirectional pulse current signals. In this case, charge compensation may be rapidly completed through multiple compensations.

In addition, in the charge compensation circuit according to the present invention, optionally, in the bidirectional pulse current signals, a waveform of a positive pulse current signal is opposite to a waveform of a negative pulse current signal; the detection circuit detects the charge amount of the positive pulse current signal and an absolute value of the charge amount of the negative pulse current signal; and the determination circuit compares the charge amount of the positive pulse current signal with the absolute value of the charge amount of the negative pulse current signal to determine whether the total charge amount exceeds the safe charge amount range.

In addition, in the charge compensation circuit according to the present invention, optionally, the detection circuit detects an average value of the bidirectional pulse current signals generated by the pulse current generation circuit; the determination circuit determines whether an absolute value of the average value is greater than a preset value; and when the absolute value of the average value is greater than the preset value, the compensation circuit generates a compensation pulse current signal with a net charge amount, so that the total charge amount is within the safe charge amount range. In this case, it can be determined conveniently whether to provide charge compensation by detecting whether the average value is greater than the preset value.

In addition, in the charge compensation circuit according to the present invention, optionally, the detection circuit detects a current average value of the bidirectional pulse current signals generated by the pulse current generation circuit, and converts the current average value into a voltage average value; the determination circuit determines whether an absolute value of the voltage average value is greater than a preset voltage value; and when the absolute value of the voltage average value is greater than the preset voltage value, the compensation circuit generates a compensation pulse current signal with a net charge amount, so that the total charge amount is within the safe charge amount range. In this case, the current average value may be converted into the voltage average value for detection; the absolute value of the voltage average value is compared with the preset voltage value; and when the absolute value of the voltage average value is greater than the preset voltage value, the total charge amount for neural stimulation is within the safe charge amount range through the compensation of the compensation circuit.

In addition, in the charge compensation circuit according to the present invention, optionally, when the absolute value of the voltage average value is greater than the preset voltage value and the voltage average value is a positive value, the compensation circuit generates a compensation pulse current signal with a negative net charge amount so that the total charge amount for neural stimulation is within the safe charge amount range; and when the absolute value of the voltage average value is greater than the preset voltage value and the voltage average value is a negative value, the compensation circuit generates a compensation pulse current signal with a positive net charge amount so that the total charge amount for neural stimulation is within the safe charge amount range.

In addition, in the charge compensation circuit according to the present invention, the preset amplitude is a minimum current amplitude which can play a stimulation effect on nerve tissue. Thus, the compensation pulse current signal can be prevented to producing a false stimulation on the nerve tissue.

In addition, a third aspect of the present invention provides a charge compensation method configured for conducting charge compensation on the pulse current generation circuit which is configured for generating bidirectional pulse current for neural stimulation. The charge compensation method includes: detecting the total charge amount during one stimulation period of the bidirectional pulse current signals generated by the pulse current generation circuit; determining that the total charge amount detected by the detection circuit is less than or equal to the safe charge amount; and generating a compensation pulse current signal with a net charge amount when the determination circuit determines that the total charge amount exceeds the safe charge amount range, so that the total charge amount is within the safe charge amount range.

In addition, in the charge compensation method according to the present invention, optionally, when the total charge amount is determined to be a positive value, a compensation pulse current signal with a negative compensation charge amount is generated so that the total charge amount is within the safe charge amount range; and when the total charge amount is determined to be a negative value, a compensation pulse current signal with a positive compensation charge amount is generated so that the total charge amount is within the safe charge amount range. Thus, the total charge amount for neural stimulation is effectively ensured to be within the safe charge amount range.

In addition, a fourth aspect of the present invention provides an implantable electrical retina stimulator, including: an implanted device having at least one of the pulse current generation circuit or the charge compensation circuit mentioned above; a video recording device configured to capture a video image and convert the video image into a visual signal; a video processing device connected with the video recording device and configured to process the visual signal to generate a modulation signal; and an analogue signal transmitting device configured to transmit the modulation signal to the implanted device, wherein the implanted device converts the received modulation signal into the bidirectional pulse current signals used as electrical stimulation signals, so as to transmit the bidirectional pulse current signals for ganglion cells or bipolar cells of the retina to generate a sense of light.

According to the present invention, a more effective stimulation effect can be generated. Moreover, a higher processing requirement, such as stimulation algorithm optimization, can be adapted at a hardware level. The charge compensation circuit actively compensates possible redundant net charge on the nerve tissue (such as ganglion cells or bipolar cells), which can improve the efficiency of charge balance on stimulation charge and ensure safety and reliability of neural stimulation. In addition, under the condition that a large capacitor with large occupied area is not used, charge balance capability can be fully enhanced within a limited space.

DETAILED DESCRIPTION

Figure 1:
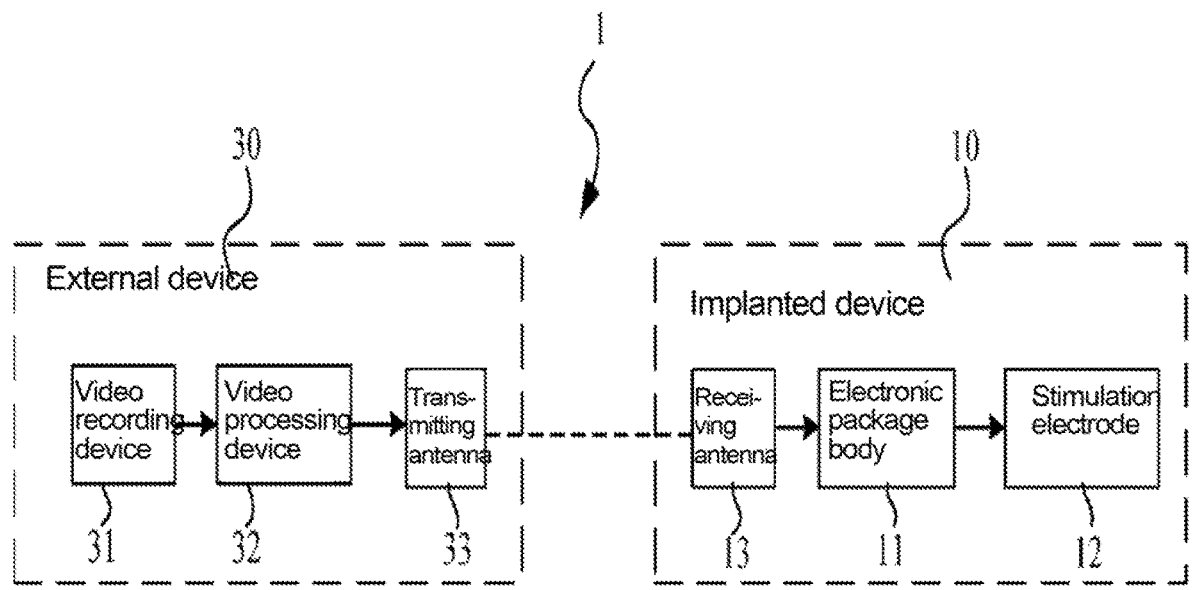
FIG. 1 is a structural schematic diagram showing an implantable electrical retina stimulator according to a first embodiment of the present invention.

Hereinafter, preferred embodiments of the present invention will be described in detail with reference to the accompanying drawings. In the following description, the same components are denoted by the same reference numerals, and the description thereof will not be repeated. In addition, the drawings are merely schematic views, and the ratio of the dimensions of the components to each other or the shapes of the components may be different from the actual ones.

First Embodiment

Figure 2:
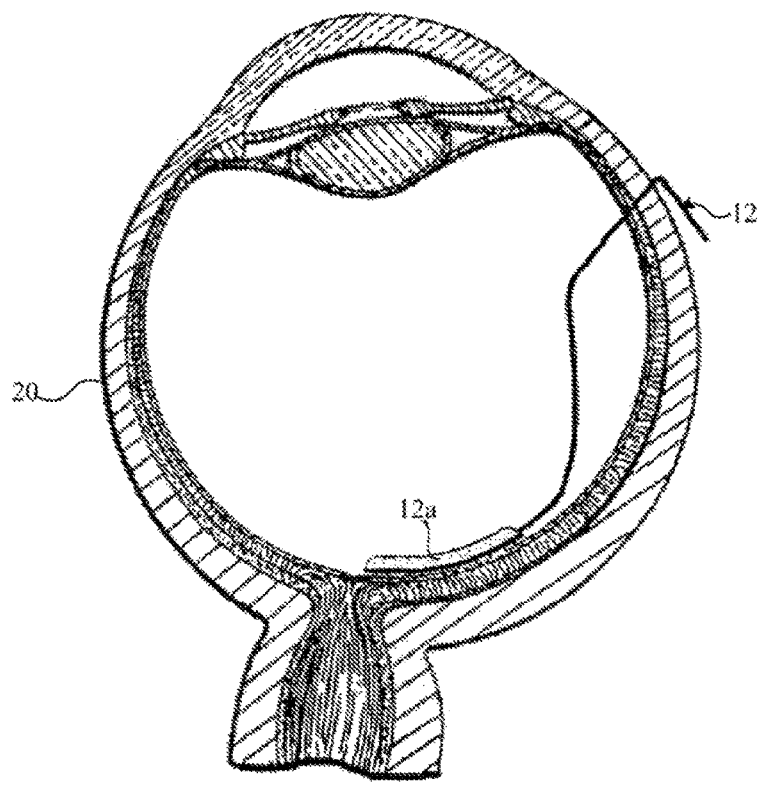
FIG. 2 is a schematic diagram showing the implantation of a stimulation electrode structure of an implantable electrical retina stimulator according to the first embodiment of the present invention into an eyeball.
Figure 3:
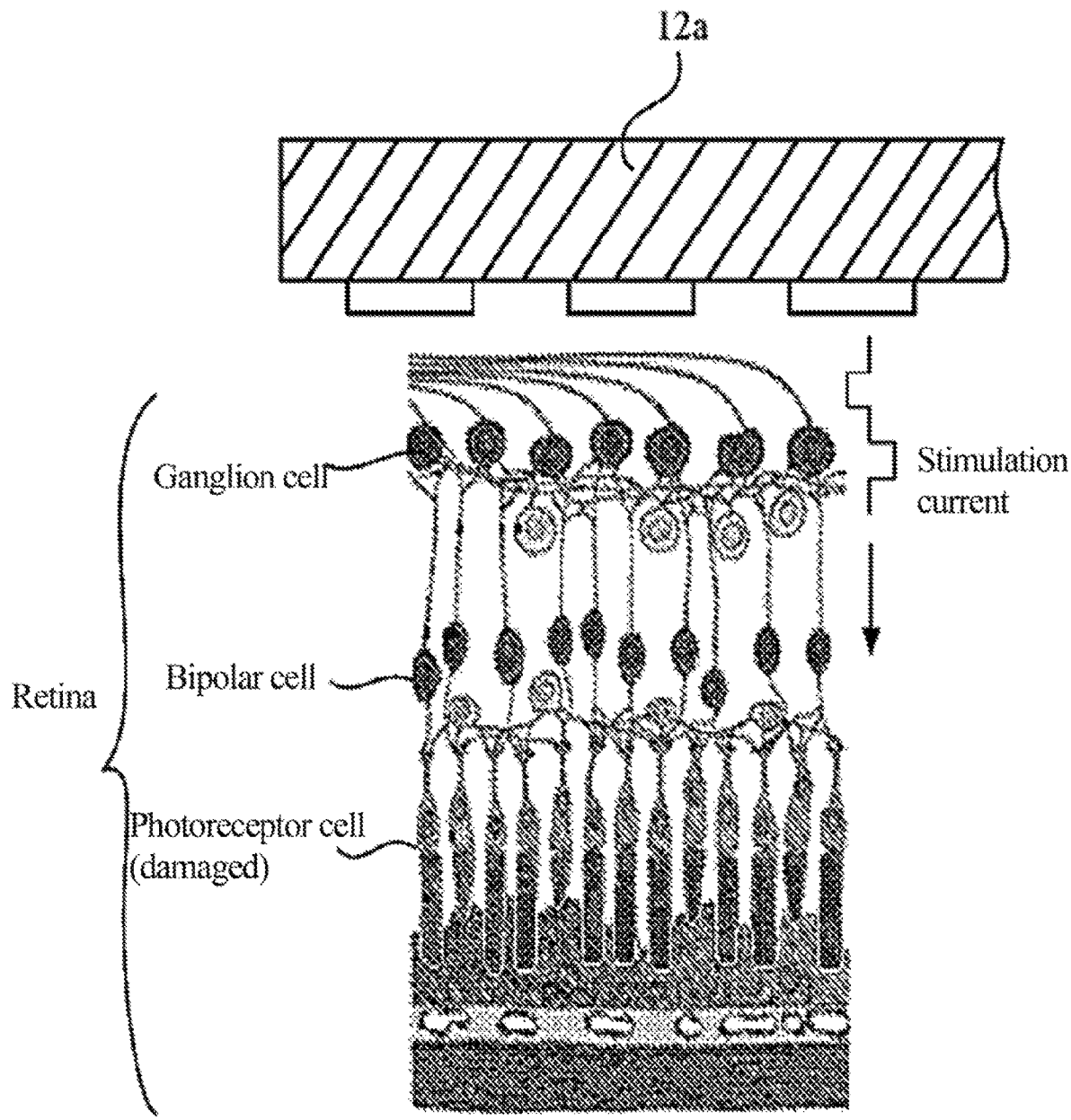
FIG. 3 is a partial schematic diagram showing the attachment of a stimulation electrode structure (a stimulation end) shown in FIG. 2 to retina in an eyeball.

FIG. 1 is a structural schematic diagram showing an implantable electrical retina stimulator according to a first embodiment of the present invention. FIG. 2 is a schematic diagram showing the implantation of a stimulation electrode structure of the implantable electrical retina stimulator according to the first embodiment of the present invention into an eyeball. FIG. 3 is a partial schematic diagram showing the attachment of the stimulation electrode structure (a stimulation end) shown in FIG. 2 to the retina in the eyeball.

In the present embodiment, as shown in FIG. 1, the implantable electrical retina stimulator (sometimes referred to as an "artificial retina" or "artificial retina system") 1 may include a part implanted into human body, i.e., an implanted device 10, and apart outside the body, i.e., an external device 30. In the implantable electrical retina stimulator according to the present embodiment, the implanted device 10 and the external device 30 may be coupled wirelessly. In some examples, the implanted device 10 and the external device 30 may be coupled by a receiving antenna 13 and a transmitting antenna 33 shown in FIG. 1. In addition, a coupling manner of the implanted device 10 and the external device 30 is not limited thereto in the present embodiment. For example, the implanted device 10 and the external device 30 may also be implemented in an infrared receiving manner.

In some examples, the implanted device 10 primarily includes a substrate (not shown) as well as an electronic package body 11, a stimulation electrode structure 12 and the receiving antenna 13 which are disposed on the substrate. In addition, the substrate in the implanted device 10 may be fixed to the eyeball 20 in, for example, a stitching manner.

Furthermore, as shown in FIG. 2, a stimulation end 12a (a stimulation electrode array) of the stimulation electrode structure 12 in the implanted device 10 may enter a vitreous cavity of the eyeball 20 via an incision of the eyeball 20, and is close to the retina so that the retina (especially ganglion cells or bipolar cells of the retina) can be stimulated electrically (for example, a bidirectional pulse current is issued) (see FIG. 3).

In general, for example, for patients with retinitis pigmentosa (RP) or age-related macular degeneration (AMD), photoreceptor cells decay or die due to the RP or AMD, i.e. normal visual pathways are hindered by the lesions of photoreceptor cell diseases, and light that normally enters eyes cannot be converted into visual electrical signals so that the patients lose the sense of sight. In the present embodiment, the stimulation end 12a of the stimulation electrode structure 12 is equivalent to replace the photoreceptor cells; and the stimulation end 12a stimulates the ganglion cells or bipolar cells of the retina (see FIG. 3) by generating electrical stimulation signals, for example, issuing the bidirectional pulse current signals Since most of the visual pathways except the photoreceptor cells are well preserved in most patients with the RP or AMD, the electrical stimulation signals are transmitted to a cerebral cortex via well-preserved downstream visual pathways (optic nerves) and generate the sense of light after the ganglion cells or bipolar cells are stimulated by electrical stimulation signals generated by the stimulation electrode structure 12 so that visions of the patients can be restored partially.

In addition, it should be noted that although the present embodiment focuses on the description of optic neural stimulation of the implantable electrical retina stimulator, the present embodiment is not limited to the field of artificial retina, and instead, the pulse current generation circuit 100 according to the present embodiment may also be applied to other neural stimulation fields such as cochlear implants, deep brain stimulation, cardiac pacemakers, spinal cord stimulators.

External Device

In the present embodiment, as shown in FIG. 1, the external device 30 may include a video recording device 31, a video processing device 32 and the transmitting antenna 33. In the external device 30, the video recording device 31 may be configured to capture a video image and convert the captured video image into a visual signal.

In some examples, the video recording device 31 may be a device having a video recording function such as a video camera, a digital camera, a CCD camera or the like. For example, an image of the outside world can be captured by the video recording device 31. Besides, for the convenience of use, a smaller video camera may be embedded in glasses. Moreover, lightweight glasses having the video recording function may be worn as the video recording device 31 to capture the video image. Furthermore, the video recording device 31 may also be implemented through Google Glass® or the like. In addition, the image may be acquired by ultrasonic imaging (for example, sonar) or electromagnetic wave imaging (for example, radar), or other devices capable of generating range and angle information in the present embodiment.

As shown in FIG. 1, the video processing device 32 is connected with the video recording device 31, and receives the visual signal supplied by the video recording device 31. After the visual signal captured by the video recording device 31 is transmitted to the video processing device 32, the video processing device 32 can process the visual signal. In some examples, the video processing device 32 may include a microprocessor, an application specific integrated circuit (ASIC), DSP, etc. to conduct image processing (such as sampling, encoding, modulation, filtration) on the visual signal. In addition, the video processing device 32 also has a power supply. The power supply may provide an energy signal to the implanted device 10, for example, in a wireless transmission manner so that the implanted device 10 implanted in the eyeball 20 is powered.

The analogue signal transmitting device (i.e., the transmitting antenna 33) may transmit the energy signal provided by the video processing device 32 and the processed visual signal as modulation signals (for example, RF modulation signals) to the implanted device 10 of the artificial retina.

In another aspect, the implanted device 10 may be configured to receive the modulation signals transmitted by the video processing device 32 via, for example, the transmitting antenna 33, and further process the modulation signals to generate the bidirectional pulse current as a stimulation current (stimulation signal) for neural stimulation.

Specifically, the receiving antenna 13 (i.e., a specific embodiment of the analogue signal receiving device 101 described later) shown in FIG. 1 receives the modulation signals and transmits the modulation signals to a subsequent electronic package body 11 for processing. Finally, the electrical stimulation signals are generated by the electronic package body 11 (specifically, a processing circuit in the electronic package body 11) according to the modulation signals and transmitted to the stimulation end 12a (for example, the stimulation electrode array) of the stimulation electrode structure 12, thereby stimulating, for example, the ganglion cells or bipolar cells of the retina (see FIG. 3). The ganglion cells or bipolar cells generate an excitation response after receiving the pulse current to generate the sense of light. In these cases, the stimulation current may stimulate the ganglion cells of the retina or the bipolar cells of the retina, and may also stimulate the ganglion cells or bipolar cells of the retina at the same time.

Pulse Current Generation Circuit

Figure 4:
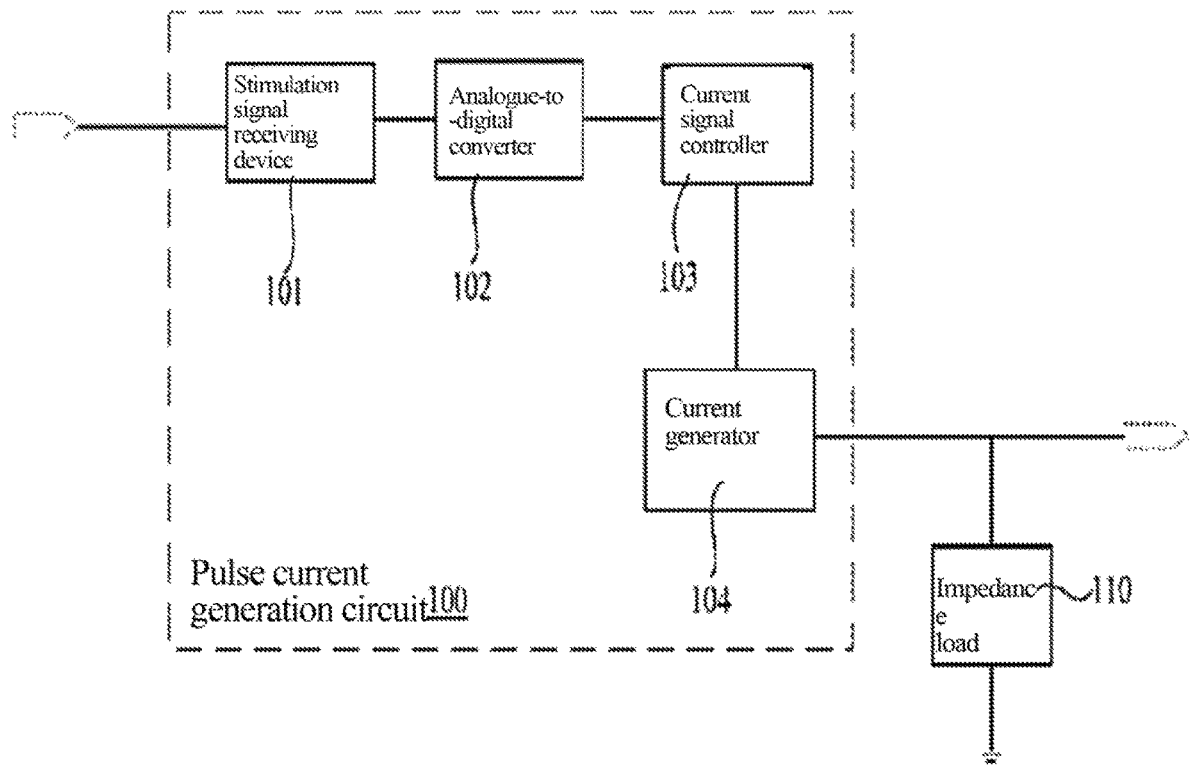
FIG. 4 is a schematic diagram showing a circuit module of a pulse current generation circuit for neural stimulation according to the first embodiment of the present invention.
Figure 5:
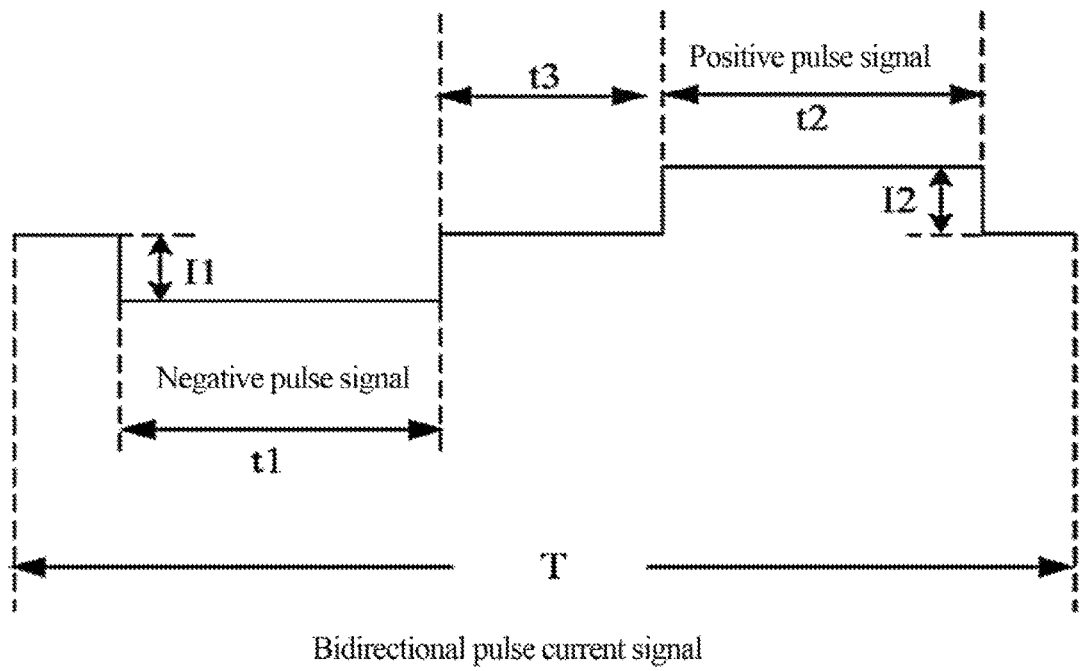
FIG. 5 is a schematic diagram showing bidirectional pulse current signals according to the first embodiment of the present invention.

FIG. 4 is a schematic diagram showing a circuit module of the pulse current generation circuit for neural stimulation according to the first embodiment of the present invention. FIG. 5 is a schematic diagram showing the bidirectional pulse current signals according to the first embodiment of the present invention.

As shown in FIG. 4, the pulse current generation circuit 100 for neural stimulation according to the present embodiment may include the analogue signal receiving device 101, an analogue-to-digital converter 102, a current signal controller 103 and a current generator 104.

In the present embodiment, the pulse current generation circuit 100 may be applied to the implantable electrical retina stimulator shown in FIG. 1. In this case, the pulse current generation circuit 100 may be located in the implanted device 10 shown in FIG. 1.

In some examples, for example, in the implanted device 10, the pulse current generation circuit 100 can generate the bidirectional pulse current signals for stimulating the ganglion cells or bipolar cells of the retina. Furthermore, in some examples, the bidirectional pulse current signals generated by the pulse current generation circuit 100 can be issued to, for example, the ganglion cells or bipolar cells of the retina by the stimulation end 12a (see FIG. 2) of the stimulation electrode structure 12 disposed in the implanted device 10.

Analogue Signal Receiving Device

In the present embodiment, the analogue signal receiving device 101 is configured to receive an analogue signal in the form of an antenna. The analogue signal receiving device 101 transmits the received analogue signal to the analogue-to-digital converter 102. As described above, the analogue signal receiving device 101 may be the receiving antenna 13 composed of receiving coils. Herein, the coils of the receiving antenna 13 may be formed by winding metal wires such as gold wires. In addition, the number of turns of the coils of the receiving antenna 13 is not particularly limited and may be set as needed.

Analogue-to-Digital Converter

The analogue-to-digital converter 102 can convert the analogue signal received by the analogue signal receiving device 101 into a digital control signal and transmit the digital control signal to the current signal controller 103. In the present embodiment, a circuit structure of the analogue-to-digital converter 102 is not particularly limited; and analogue-to-digital converters with different resolutions such as 4 bits, 6 bits, 8 bits, 10 bits, 14 bits, 16 bits, etc. may be used as needed. In addition, the analogue-to-digital converter 102 may be a successive approximation type analogue-to-digital converter, a parallel comparison type analogue-to-digital converter, or an integral type analogue-to-digital converter. In addition, the digital control signal may be a series of digital signal streams, which indicate pulse current parameters of the bidirectional pulse current signals to be generated subsequently.

Current Signal Controller

The current signal controller 103 may produce the pulse current parameters for generating the bidirectional pulse current signals according to the digital control signal outputted by the analogue-to-digital converter 102. Herein, the bidirectional pulse current as the stimulation signal may include a positive pulse current and a negative pulse current. For the neural stimulation field, the charge of the positive pulse current of the bidirectional pulse current and the charge of the negative pulse current generally need to be equal to ensure the safety when nerve tissue is stimulated. The effect of the bidirectional pulse current on the neural stimulation will be described in more detail later.

In some examples, the bidirectional pulse current may be a bidirectional pulse current of square waveform. In this case, the pulse current parameters of the bidirectional pulse current may include a negative pulse width t1, a negative pulse amplitude I1, a positive pulse width t2, a positive pulse amplitude I2 and a pulse interval t3 (see FIG. 5). Herein, the pulse interval t3 refers to a time interval between a negative pulse and a positive pulse. In addition, the time T is a stimulation period T described later.

As described above, the current signal controller 103 may produce the pulse current parameters for generating the bidirectional pulse current signals according to the digital control signal. In some examples, the digital control signal can instruct the current controller 103 to generate the bidirectional pulse current having a wider negative pulse width t1 (for example, t1>t2). In other examples, the digital control signal may instruct the current controller 103 to generate the bidirectional pulse current having a smaller negative pulse amplitude I1 (for example, I1<I2).

Current Generator

The current generator 104 may generate the bidirectional pulse current signals for neural stimulation according to the pulse current parameters. In the present embodiment, since the pulse current generation circuit 100 for neural stimulation can maintain the high precision of the pulse current while increasing the width of the stimulation pulse current, a more effective current stimulation effect can be provided, for example, the bipolar cells of the retina can be stimulated effectively. In another aspect, since a wider pulse modulation range can be realized, higher processing requirements such as stimulation algorithm optimization can be adapted at a hardware level.

In the present embodiment, the current generator 104 may generate at least two pulse currents of different precision according to the pulse current parameters. In some examples, the current generator 104 can generate two pulse currents of different precision. In other examples, the current generator 104 can generate three, four, five or more than five pulse currents of different precision. In addition, the different precision multiples between the adjacent different pulse currents may be twice, for example, in the situation that current generator 104 generates five pulse currents of different precision including a first pulse current, a second pulse current, a third pulse current, a fourth pulse current and a fifth pulse current, the precision of the fifth pulse current is twice the precision of the fourth pulse current, the precision of the fourth pulse current is twice the precision of the third pulse current, the precision of the third pulse current is twice the precision of the second pulse current, and the precision of the second pulse current is twice the precision of the first pulse current. In addition, the present embodiment is not limited thereto, and other pulse currents of different precisions may also be adopted.

Impedance Load

As shown in FIG. 4, when the current generator 104 conducts neural stimulation on the nerve tissue or the like, the impedance load 110 is connected equivalently. For example, when the pulse current generation circuit 100 according to the present embodiment is configured for neural stimulation of the artificial retina, the ganglion cells or bipolar cells of the retina in the human tissue fluid may be simplistically equivalent to the impedance load 110.

Figure 6:
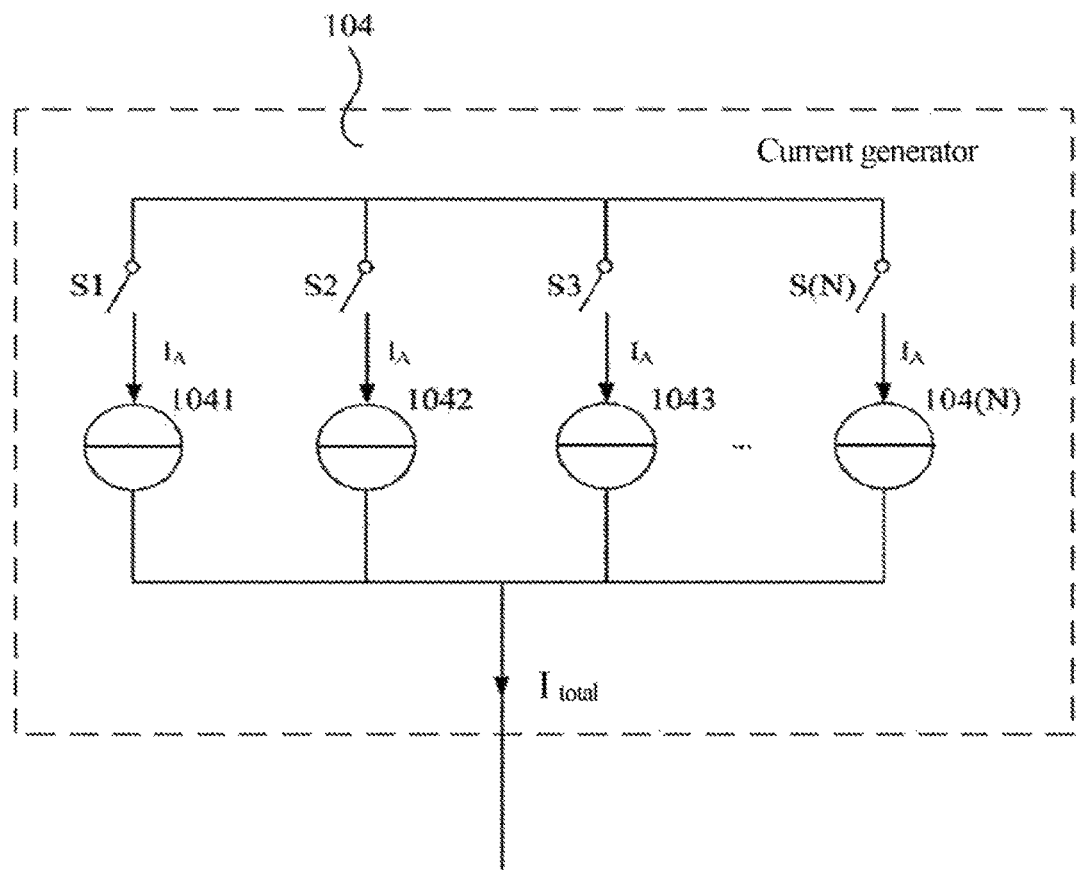
FIG. 6 is a schematic diagram showing a circuit module of a current generator according to the first embodiment of the present invention.
Figure 7:
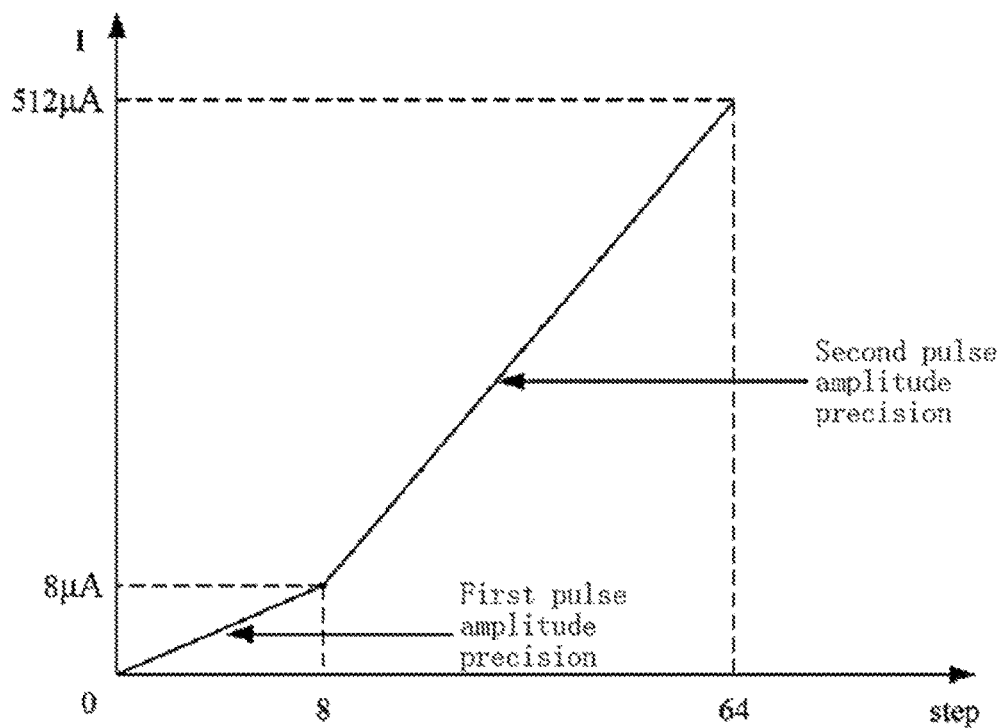
FIG. 7 is a schematic diagram showing precisions of different pulse current amplitudes according to the first embodiment of the present invention.
Figure 8:
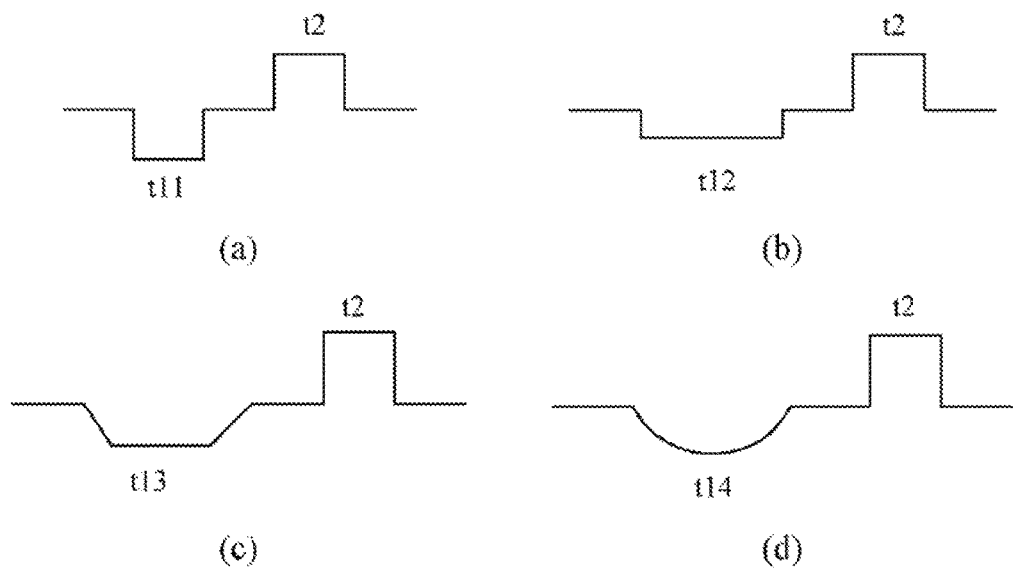
FIGS. 8a to 8d are schematic diagrams showing stimulation waveforms of different bidirectional pulse currents.

Hereinafter, the current generator 104 according to the present embodiment will be described in more detail with reference to FIG. 6 and FIG. 7. FIG. 6 is a schematic diagram showing a circuit module of the current generator according to the first embodiment of the present invention. FIG. 7 is a schematic diagram showing the precisions of different pulse current amplitudes according to the first embodiment of the present invention. FIGS. 8a to 8d are schematic diagrams showing stimulation waveform of different bidirectional pulse currents.

As shown in FIG. 6, the current generator 104 may include N current sources. In some examples, the N current sources may be composed of one reference current source 1041 and (N−1) mirror current sources (current source arrays). The current sources, for example, are respectively controlled by a switch S1, a switch S2, . . . , and a switch S(N). Herein, the switch S1, the switch S2, . . . , and the switch S(N) control the amplitude of the total pulse current generated by the current generator 104, i.e., the pulse amplitude (positive or negative pulse amplitude) of the total pulse current is proportional to the number of closed switches S(N), wherein the switch S1 controls the reference current source 1041. In this case, the total current amplitude Itotal generated by the current generator 104 is equal to (the number of closed switches+1) multiplied by the current amplitude of the reference current source.

When the current generator 104 is composed of the N current sources mentioned above, the magnitude of the pulse current may be determined by the opening and closing of (N+1) current sources, and the precision of the pulse current may be determined by the size of the reference current source 1041. Specifically, the magnitude of the reference current source 1041 is the magnitude of the precision of the pulse current. For example, if the reference current source 1041 is 1 μA (microamperes), the precision of the pulse current is 1 μA, and a current value of each mirror current source in (N−1) mirror current sources, i.e., a current source 1042, a current source 1043, . . . , and a current source 104(N) is the same as the current value of the reference current source 1041. After the magnitude of the reference current source 1041 is set, the current value of each mirror current source in the current source 1042, the current source 1043, . . . , and the current source 104(N) is equal to the reference current source 1041.

In some examples, if the number of the reference current sources 1041 and the (N−1) mirror current sources is N=512 in total, and the precision of the reference current source 1041 is set to 1 μA, the current generator 104 may generate a pulse current having the precision of 1 μA and 512 pulse amplitudes, i.e., the current generator 104 may generate a total of 512 different current amplitudes including 1 μA, 2 μA, 3 μA, . . . , and 512 μA by controlling the switch S1, the switch S2, . . . , and the switch S(N). In other examples, if the number of the reference current sources 1041 and the (N−1) mirror current sources is N=512 in total, and the precision of the reference current source 1041 is set to 4 μA, the current generator 104 may generate a pulse current having the precision of 4 μA and 128 pulse amplitudes, i.e., the current generator 104 may generate a total of 128 different current amplitudes including 4 μA, 8 μA, 12 μA, . . . , and 512 μA by controlling the switch S1, the switch S2, . . . , and the switch S(N). In some other examples, if the number of the reference current sources 1041 and the (N−1) mirror current sources is N=512 in total, and the precision of the reference current source 1041 is set to 8 μA, the current generator 104 may generate a pulse current having the precision of 8 μA and 64 pulse amplitudes, i.e., the current generator 104 may generate a total of 64 different current amplitudes including 8 μA, 16 μA, 24 μA, . . . , and 512 μA by controlling the switch S1, the switch S2, . . . , and the switch S(N). Although the current precisions 1 μA, 4 μA and 8 μA are introduced as examples in the above description, the present embodiment is not limited thereto, and the pulse current generation circuit 100 according to the present embodiment may also generate currents having, for example, 2 μA, 6 μA, 12 μA and other precisions.

As described above, since different current precisions may be realized by setting the reference current sources 1041 of different current magnitudes, the precisions of the generated pulse currents can be set by setting a plurality of different reference current sources in the present embodiment, so that a plurality of pulse currents of different precisions can be generated. In the present embodiment, two different reference current sources may be set, and pulse currents of two different precisions (high precision and low precision) may be realized in this case.

In some examples, the current generator 104 may generate the bidirectional pulse currents of two different precisions including a first pulse amplitude precision (high precision) and a second pulse amplitude precision (low precision). For example, a first pulse amplitude precision may be set to 1 μA/step, the range of current amplitude is 0-8 μA; and a second pulse amplitude precision may be set to 8 μA/step, the range of current amplitude is 8-512 μA (see FIG. 7). Herein, the precision (the first pulse amplitude precision is 1 μA/step) of the pulse amplitude of the high-precision pulse current is greater than the precision (the second pulse amplitude precision is 8 μA/step) of the pulse amplitude of the low-precision pulse current. Thus, the current generator 104 may generate the pulse currents of different precisions according to actual conditions to meet the requirements of different neural stimulation signals. In addition, in other examples, the current generator 104 may provide more pulse currents of different precisions.

Bidirectional Pulse Current Signals

In some examples, the total charge amount during one stimulation period T of the bidirectional pulse current signals generated by the current generator 104 is within the safe charge amount range (for example, the total charge amount is zero). Specifically, in the neural stimulation field, in order to prevent the pulse current signal from generating a net charge on human nerve tissue such as ganglion cells or bipolar cells of the retina to damage the human nerve tissue, it should be ensured that the total charge amount of the bidirectional pulse current signals during one stimulation period T is within the safe charge amount range.

Herein, the "safe charge amount" is the maximum value of the net charge which can be withstood by the nerve tissue (for example, the ganglion cells or bipolar cells of the retina) within a safe range. The net charge exceeding the safe charge amount range may cause damage to the nerve tissue. Herein, one stimulation period T is a period time at which a stimulation signal is generated. Therefore, during actual neural stimulation, it should be ensured that the total charge amount during one stimulation period T is controlled within the safe charge amount range. Herein, one stimulation period T is a period time at which a stimulation signal is generated. The total charge amount refers to the total charge amount of the net charge of the bidirectional pulse current signals during one stimulation period T. In some examples, the safe charge amount may also be set to zero for convenience.

In addition, in the present embodiment, if it is ensured that the total charge amount of the bidirectional pulse current during one stimulation period T is within the safe charge amount range, the waveform of the pulse current is not limited. FIGS. 8a-8d show schematic diagrams of stimulation waveforms of different bidirectional pulse currents. Since the negative pulse current is usually used as an effective stimulation signal in the neural stimulation field, modified examples of the bidirectional pulse current signals are illustrated by taking the negative pulse waveform as an example in FIGS. 8a-8d.

As shown in FIGS. 8a-8d, for the bidirectional pulse current signals as the stimulation waveforms, the waveform of the negative pulse and the waveform of the positive pulse are not necessarily the same, but it is ensured that the total charge amount of the bidirectional pulse current signals during one stimulation period T is within the safe charge amount range. As an example, the negative pulse widths t11, t12, t13 and t14 may each be greater than the positive pulse width t2, thereby realizing a wide stimulation pulse. In addition, the bidirectional pulse current may be a bidirectional square wave pulse current signal, or a cosine pulse current signal, or a combination of the square wave pulse current signal and the cosine pulse current signal.

As described above, the current generator 104 may generate the bidirectional pulse current signals according to the pulse current parameters. Specifically, the bidirectional pulse current signals may include effective stimulation current signals and balanced current signals, wherein the effective stimulation current signals are current signals having a stimulating effect on neural stimulation objects such as the ganglion cells or bipolar cells; and the balanced current signals are current signals for balancing the charge generated by the effective stimulation current signals. Generally, if the effective stimulation signals are positive pulses, the balanced current signals are negative pulses; if the effective stimulation signals are negative pulses, the balanced current signals are positive pulses. Thus, it can be ensured that the total charge amount of the bidirectional pulse current signals during one stimulation period T is within the safe charge amount range. (For example, the total charge amount is zero).

In the present embodiment, as described above, the current signal controller 103 produces the pulse current parameters for generating the bidirectional pulse current signals Thus, the total charge amount of the bidirectional pulse current signals theoretically generated by the current generator 104 during one stimulation period is within the safe charge amount range by setting the pulse current parameters. In addition, in order to suppress the influence of the net charge which may be accumulated by the stimulation current signals on a human body, the bidirectional pulse current signals are usually set such that only one of the positive pulse and the negative pulse is the stimulation signal, and the other is the balanced current signal. Thus, it is ensured that the total charge amount of the bidirectional pulse current signals during one stimulation period T is within the safe charge amount range.

As a specific example, during one stimulation period T, an integral of the negative pulse signal of the bidirectional pulse current signals in time may be equal to an absolute value of the integral of the positive pulse signal of the bidirectional pulse current signals in time. Thus, the total charge amount of the bidirectional pulse current signals during one stimulation period T is within the safe charge amount range. In addition, with reference to FIG. 5, as shown in FIG. 5, during one stimulation period T, if the duration of the negative pulse signal (the negative pulse width) is t1, and the duration of the positive pulse signal (the positive pulse width) is t2, the absolute value of the integral of the negative pulse in the duration t1 is equal to the absolute value of the integral of the positive pulse in the duration t2, i.e., the total charge amount of the bidirectional pulse current signals is within the safe charge amount range (for example, the total charge amount is zero).

As described above, the current generator 104 provides two different pulse amplitude precisions including a first pulse amplitude precision and a second pulse amplitude precision, wherein the first pulse amplitude precision is 1 μA/step, and the amplitude range is 0-8 μA (for example, 1 μA, 2 μA, 3 μA, . . . , and 8 μA); the second pulse amplitude precision is 8 μA/step, and the amplitude range is 8-512 μA (for example, 8 μA, 16 μA, 24 μA, . . . , and 512 μA) (see FIG. 7).

In some examples, as shown in FIG. 7, when the neural stimulation objects such as the ganglion cells or bipolar cells of the retina require a lower pulse current stimulation, the current generator 104 may provide a higher pulse amplitude precision (for example, 1 μA/step). For example, when the current amplitude required by the ganglion cells or bipolar cells is less than or equal to 8 μA, the current has the pulse amplitude precision of 1 μA/step and is capable of providing a total of 8 pulse amplitudes including 1 μA, 2 μA, 3 μA, 4 μA, 5 μA, 6 μA, 7 μA and 8 μA; and when the current required by the ganglion cells or bipolar cells is greater than 8 μA, the current has the pulse amplitude precision of 8 μA/step and is capable of providing a total of 64 pulse amplitudes including 16 μA, 24 μA, 32 μA, 40 μA, . . . 512 μA.

In the present embodiment, the current generator 104 may provide pulse amplitudes of at least two different precisions and generate pulse currents of at least two different precisions, thereby, a more efficient current stimulation manner can be provided.

In some examples, the current generator 104 may generate the low-precision pulse current or the high-precision pulse current according to the pulse current parameters. Specifically, the current generator 104 determines whether the pulse amplitude of the bidirectional pulse current signals to be generated is less than a critical value after receiving the pulse current parameters. When the pulse amplitude of the bidirectional pulse current signals to be generated is less than or equal to the critical value, the current generator 104 generates the high-precision pulse current; and when the pulse amplitude of the bidirectional pulse current signals to be generated is greater than the critical value the current generator 104 generates the low-precision pulse current. Thus, the current generator 104 may generate corresponding pulse currents under different conditions to meet the requirements of different neural stimulation signals.

In the present embodiment, the critical value may be set in advance. In addition, the amplitude precision of the high-precision pulse current and the amplitude precision of the low-precision pulse current may also be set in advance. For example, as shown in FIG. 7, the critical value may be set to 8 μA, the amplitude precision of the high-precision pulse current is 1 μA/step, and the amplitude precision of the low-precision pulse current is 8 μA/step.

In this case, when the current generator 104 determines that the amplitude of the bidirectional pulse current signals to be generated is less than or equal to 8 μA, the current generator 104 generates the high-precision (1 μA/step) pulse current; and when the current generator 104 determines that the amplitude of the bidirectional pulse current signals to be generated is greater than 8 μA, the current generator 104 generates the low-precision (8 μA/step) pulse current. In this way, the current generator 104 may provide the pulse currents of two different precisions. When the ganglion cells or bipolar cells require a smaller pulse current, the high-precision pulse current is provided so that the bipolar cells of the retina can be stimulated more accurately, and the more efficient stimulation manner can be provided.

In some examples, when the positive pulse width of the bidirectional pulse current signals is greater than a preset duration and the positive pulse amplitude is less than the critical value, or when the negative pulse width of the bidirectional pulse current signals is greater than the preset duration and the negative pulse amplitude is less than the critical value, the current generator 104 generates the high-precision pulse current.

For the width (stimulation time) of the stimulation pulse current, although the action mechanism is still unclear, deeper nerve cells are more likely stimulated by extending the stimulation pulse width (for example, the negative pulse width), thereby, more efficient neural stimulation can be acquired. For example, for the implantable electrical retina stimulator, a wide stimulation pulse can stimulate the bipolar cells of the retina more effectively, thereby, more effective and more precise neural stimulation can be provided.

Specifically, when the negative pulse width of the bidirectional pulse current signals is greater than the preset duration and the negative pulse amplitude is less than the critical value, the bidirectional pulse current signals can stimulate the bipolar cells of the retina more precisely. Since the one-to-one correspondence of the bipolar cells in the visual pathways is superior to that of the ganglion cells, the precise stimulation of the bipolar cells may form a more accurate sense of light. In addition, higher processing requirements such as stimulation algorithm optimization can also be adapted at a hardware level.

In this way, when the positive pulse width of the bidirectional pulse current signals is greater than the preset duration and the positive pulse amplitude is less than the critical value, or when the negative pulse width of the bidirectional pulse current signals is greater than the preset duration and the negative pulse amplitude is less than the critical value, the current generator 104 generates the high-precision pulse current for precisely stimulating the bipolar cells to form a more accurate sense of light, thereby providing a more efficient stimulation manner for the blind.

Second Embodiment

Figure 9:
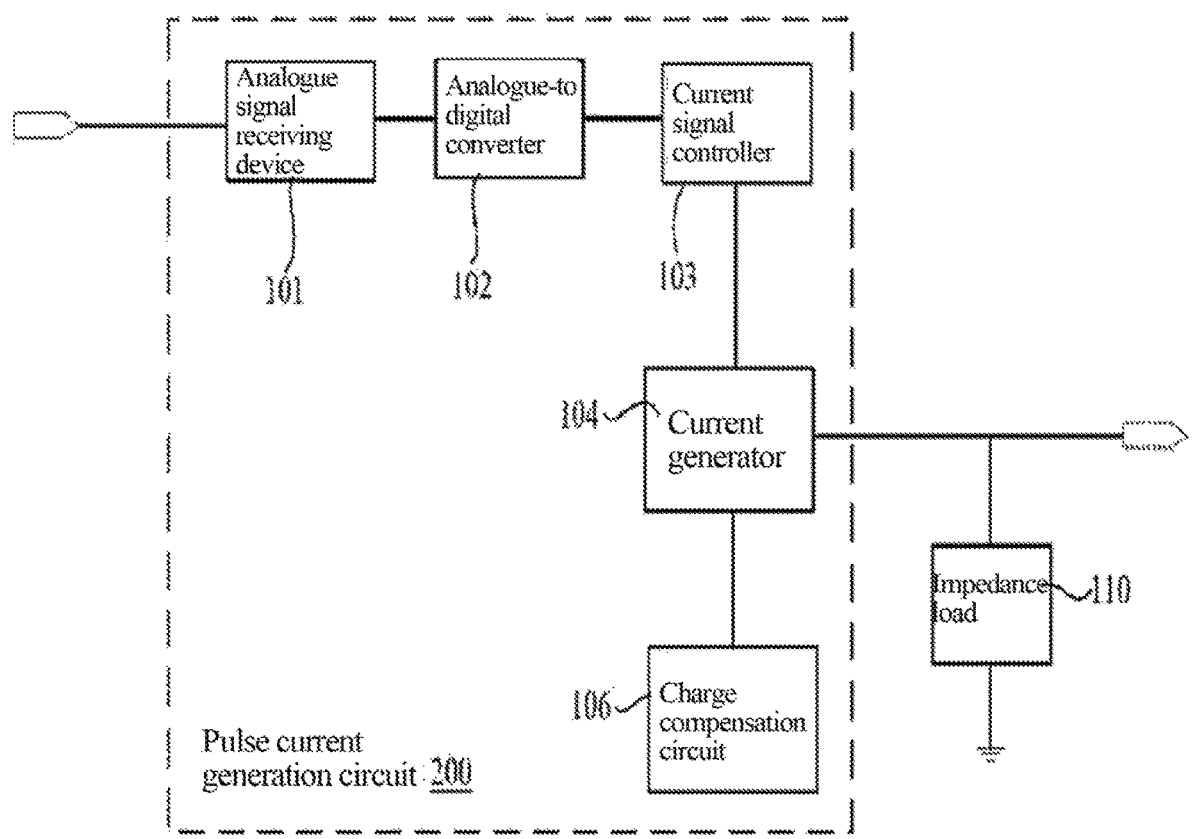
FIG. 9 is a structural schematic diagram showing a pulse current generation circuit according to the second embodiment of the present invention.
Figure 10:
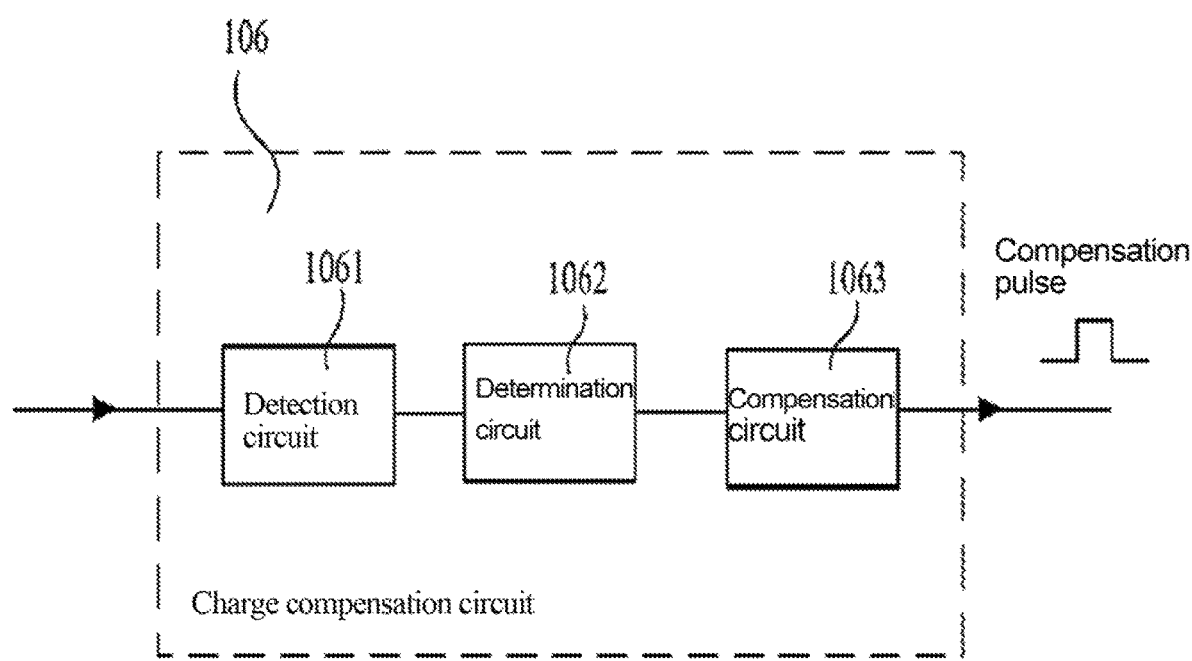
FIG. 10 is a structural schematic diagram showing a charge compensation circuit according to the second embodiment of the present invention.
Figure 11:
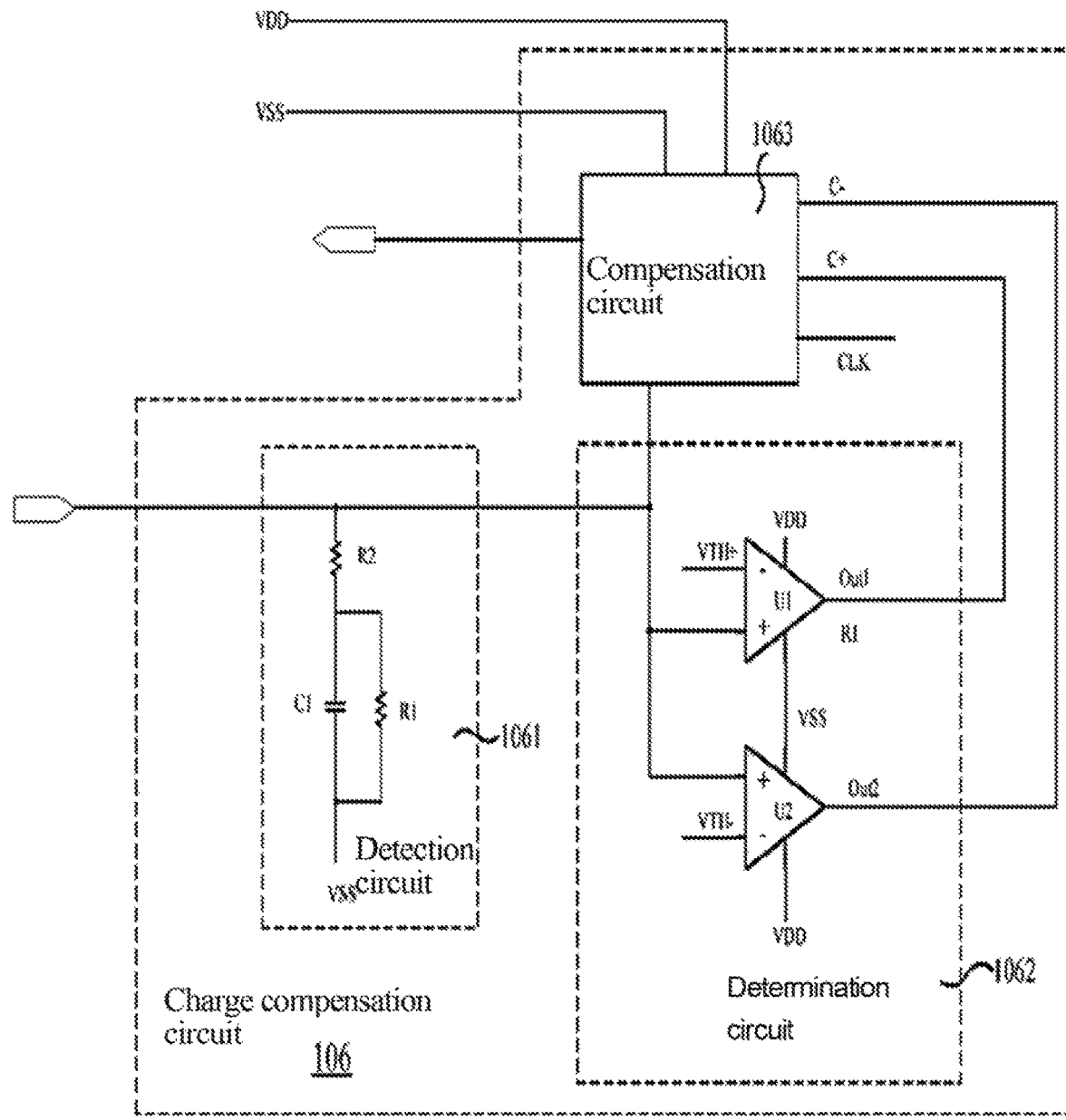
FIG. 11 is a schematic diagram showing a compensation pulse current according to the second embodiment of the present invention.
Figure 12:
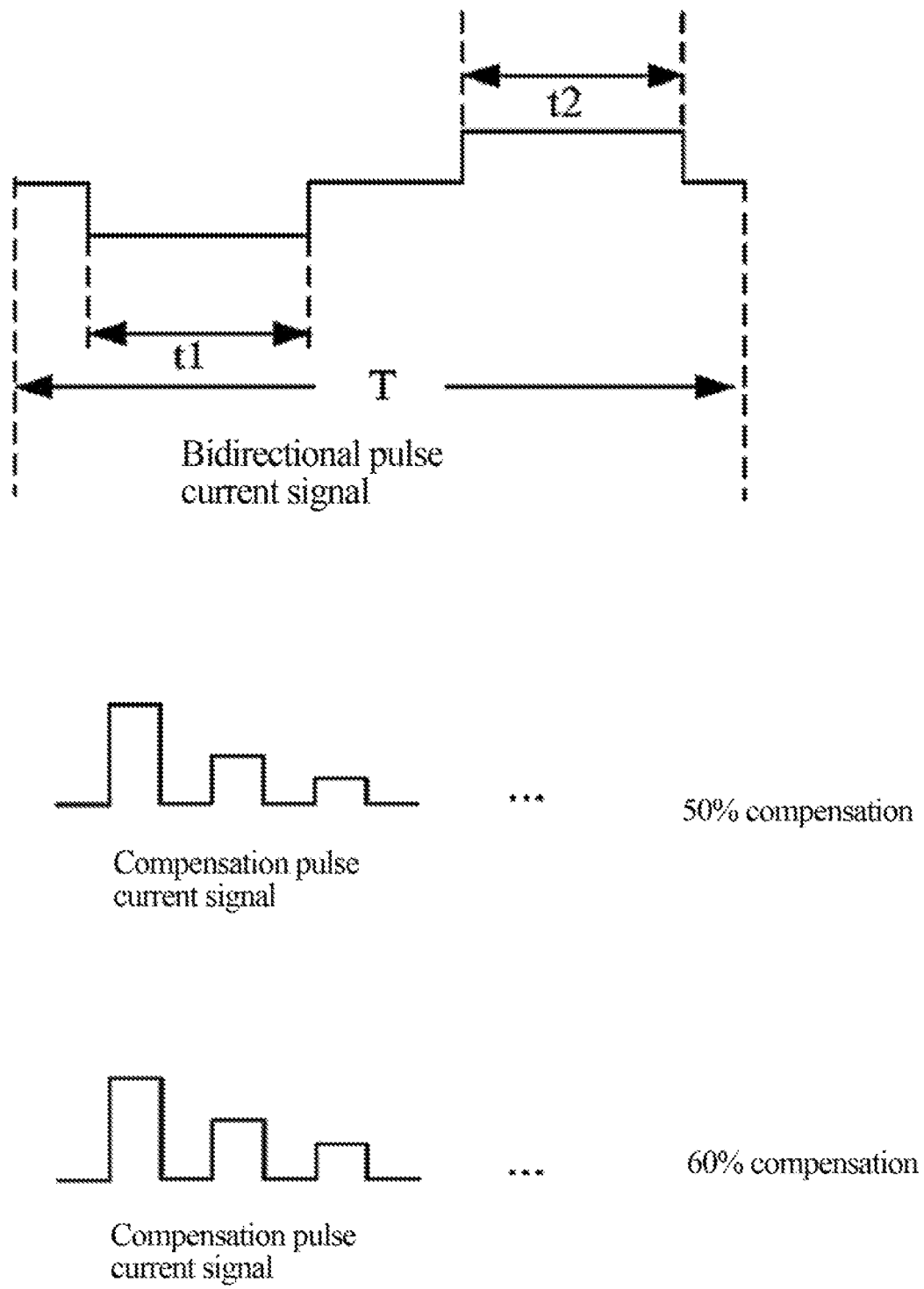
FIG. 12 is a schematic diagram showing a circuit structure of a charge compensation circuit according to the second embodiment of the present invention.

FIG. 9 is a schematic diagram showing a circuit structure of a pulse current generation circuit according to the second embodiment of the present invention. FIG. 10 is a schematic diagram showing a circuit structure of a charge compensation circuit according to the second embodiment of the present invention. FIG. 11 is a schematic diagram showing a compensation pulse current according to the second embodiment of the present invention. FIG. 12 is a schematic diagram showing a circuit structure of the charge compensation circuit according to the second embodiment of the present invention.

The pulse current generation circuit 200 according to the second embodiment differs from the pulse current generation circuit 100 according to the first embodiment in that besides the analogue signal receiving device 101, the analogue-to-digital converter 102, the current signal controller 103 and the current generator 104 according to the first embodiment, the charge compensation circuit 106 is also included.

Furthermore, it should be noted that although the present embodiment focuses on the description of the visual stimulation of the implantable electrical retina stimulator, however, the present embodiment is not limited to the field of artificial retina, and instead, the charge compensation circuit 106 according to the present embodiment may also be applied to other neural stimulation fields such as cochlear implants, deep brain stimulation, cardiac pacemakers, spinal cord stimulators.

As shown in FIG. 9, the charge compensation circuit 106 for neural stimulation is according to the present embodiment. In the present embodiment, the charge compensation circuit 106 can be applied to the implantable electrical retina stimulator shown in FIG. 1. In this case, the charge compensation circuit 106 may be located in the implanted device 10 (for example, within the electronic package body 11) shown in FIG. 1. Specifically, the pulse current generation circuit 200 may be located in the electronic package body 11 shown in FIG. 1. In the present embodiment, the charge compensation circuit 106 may be configured to conduct charge compensation on the pulse current generation circuit 200.

In the present embodiment, as shown in FIG. 10, the charge compensation circuit (also referred to as "active charge compensation circuit") 106 includes a detection circuit 10621, a determination circuit 1062 and a compensation circuit 1063. The detection circuit 1061 may be configured to detect a total charge amount during one stimulation period T of the bidirectional pulse current signals generated by the pulse current generation circuit 200.

In addition, the determination circuit 1062 may be configured to determine whether the total charge amount detected by the detection circuit 1061 exceeds the safe charge amount range. Furthermore, the compensation circuit 1063 may be configured to generate a compensation pulse current signal with a net charge amount when the determination circuit 1062 determines that the total charge amount exceeds the safe charge amount range so that the total charge amount for neural stimulation is within the safe charge amount range. Herein, the net charge amount may be a negative charge amount or a positive charge amount based on the case where compensation is required.

Theoretically, the pulse current parameters (for example, the pulse current parameters may include a positive pulse width, a positive pulse amplitude, a positive pulse amplitude, a negative pulse width, a negative pulse amplitude, a pulse interval, etc.) of the bidirectional pulse current signals can be set such that the total charge amount of the bidirectional pulse current signals during one stimulation period T is within the safe charge amount range. However, in an actual application circuit, the total charge amount of the bidirectional pulse current signals generated by the pulse current generation circuit 200 during one stimulation period T is likely to exceed the safe charge amount range due to various factors. In this case, the net charge accumulated by the bidirectional pulse current signals may cause damage to the ganglion cells or bipolar cells of human eyes.

In the present embodiment, redundant net charge accumulated on nerve tissue (for example, the ganglion cells or bipolar cells) is actively compensated by the charge compensation circuit 106 so that the ability to balance the stimulation charge can be improved and the safety and reliability of neural stimulation can be ensured, thereby playing a role of protecting human nerve tissue such as the ganglion cells or bipolar cells of the retina.

In the present embodiment, the detection circuit 1061 can be configured to detect the total charge amount during one stimulation period T of the bidirectional pulse current signals generated by the pulse current generation circuit 200. Next, the determination circuit 1062 determines whether the total charge amount during one stimulation period T of the bidirectional pulse current signals detected by the detection circuit 1061 exceeds the safe charge amount range. If the total charge amount during one stimulation period T of the bidirectional pulse current signals is within the safe charge amount range, the compensation circuit 1063 does not work; and if the total charge amount during one stimulation period T of the bidirectional pulse current signals exceeds the safe charge amount range, the compensation circuit 1063 generates a compensation pulse current signal with a net charge amount, so that the total charge amount for neural stimulation is within the safe charge amount range.

Specifically, when the determination circuit 1062 determines that the total charge amount during one stimulation period T of the bidirectional pulse current signals is a positive charge, the compensation circuit 1063 produces a negative current pulse so that the total charge amount for neural stimulation is within the safe charge amount range. When the determination circuit 1062 determines that the total charge amount during one stimulation period T of the bidirectional pulse current signals is a negative charge, the compensation circuit 1063 produces a positive current pulse so that the total charge amount for neural stimulation is within the safe charge amount range.

In the present embodiment, the compensation circuit 1063 may actively conduct charge compensation. Once the determination circuit 1062 determines that the total charge amount during one stimulation period produced by the pulse current generation circuit 200 and detected by the detection circuit 1061 exceeds the safe charge amount range, the compensation circuit 1063 may conduct charge compensation in time, thereby enhancing charge balance efficiency or capability and ensuring safety of the stimulated nerve tissue.

In some examples, the compensation circuit 1063 may generate a compensation pulse current signal with a net charge amount when the determination circuit 1062 determines that the total charge amount during one stimulation period T of the bidirectional pulse current signals exceeds the safe charge amount range, so that the total charge amount for neural stimulation is within the safe charge amount range. In addition, the compensation circuit 1063 may generate a compensation pulse current signal with a positive net charge amount when the determination circuit 1062 determines that the total charge amount during one stimulation period T of the bidirectional pulse current signals is less than zero, so that the total charge amount for neural stimulation is within the safe charge amount range.

For example, when the determination circuit 1062 determines that the total charge amount during one stimulation period T of the bidirectional pulse current signals is negative charge of $-1 \times 10^{-7}$ coulombs, the compensation circuit 1063 produces positive charge with a total charge amount of $1 \times 10^7$ coulombs (for example, the compensation circuit 1063 may produce a positive pulse with a pulse width of 1 millisecond and a pulse amplitude of 100 microamps, or the compensation circuit 1063 may produce a positive pulse with a pulse width of 10 milliseconds and a pulse amplitude of 10 microamps), so that the total charge amount for neural stimulation is within the safe charge amount range. For example, when the determination circuit 1062 determines that the total charge amount during one stimulation period T of the bidirectional pulse current signals is positive charge of $1 \times 10^{-7}$ coulombs, the compensation circuit 1063 produces negative charge with a total charge amount of $-1 \times 10^{-7}$ coulombs (for example, the compensation circuit 1063 may produce a negative pulse with a pulse width of 1 millisecond and a pulse amplitude of 100 microamps, or the compensation circuit 1063 may produce a negative pulse with a pulse width of 10 milliseconds and a pulse amplitude of 10 microamps), so that the total charge amount for neural stimulation is within the safe charge amount range.

In the present embodiment, the amplitude of the compensation pulse current signal may be lower than a preset amplitude, and the period of the compensation pulse current signal may be less than the period of the bidirectional pulse current signals. Herein, the preset amplitude is a minimum current amplitude which can play a stimulation effect on nerve tissue (such as ganglion cells or bipolar cells). The amplitude of the compensation pulse current signal is set to be lower than the preset amplitude so as to prevent the compensation pulse current signal from producing a false stimulation on the nerve tissue (such as ganglion cells or bipolar cells) and inhibiting the nerve tissue (such as ganglion cells or bipolar cells) from producing unnecessary excitement due to possible reception of the compensation pulse current signal. In addition, the period of the compensation pulse current signal may also be set to be less than the period of the bidirectional pulse current signals. Thus, charge compensation may be conducted within short time. For example, charge compensation may be conducted rapidly through multiple compensations.

In some examples, in the bidirectional pulse current signals, a waveform of a positive pulse current signal may be opposite to a waveform of a negative pulse current signal. Namely, in the bidirectional pulse current signals, the waveform of the pulse currents are identical except that the waveform of the positive pulse current signal is opposite to the waveform of the negative pulse current signal. In this way, the detection circuit 1061 may detect the charge amount of the positive pulse current signal and an absolute value of the charge amount of the negative pulse current signal. Then, the determination circuit 1062 compares the charge amount of the positive pulse current signal with the absolute value of the charge amount of the negative pulse current signal to determine whether the total charge amount exceeds the safe charge amount range.

Again referring to FIG. 5, FIG. 5 is a schematic diagram showing bidirectional pulse current signals according to the embodiment of the present invention. As shown in FIG. 5, the bidirectional pulse current signals may include a positive pulse signal and a negative pulse signal, and the waveform of the positive pulse current signal is opposite to the waveform of the negative pulse current signal. At this moment, the detection circuit 1061 may detect the charge amount of the positive pulse current signal and the absolute value of the charge amount of the negative pulse current signal. For example, the charge amount of the positive pulse current signal is $Q1=I1 \times t1$, and the absolute value of the charge amount of the negative pulse current signal is $Q2=|I2 \times t2|$, and $|I2 \times t2|$ is the absolute value of $I2 \times t2$. Next, the determination circuit 1062 determines a difference between the charge amount Q1 and the charge amount Q2, i.e., the total net charge amount=Q1-Q2. When the charge amount Q1 is equal to the charge amount Q2, the total charge amount is determined to be zero. When the charge amount Q1 is not equal to the charge amount Q2, the total charge amount is determined not to be zero, wherein when the charge amount Q1 is greater than the charge amount Q2, the total charge amount is determined to be a positive value (there is a positive net charge); and when the charge amount Q1 is less than the charge amount Q2, the total charge amount is determined to be a negative value (there is a negative net charge). In addition, the above total charge amount shall be ensured to be within the safe charge amount range regardless of the positive net charge and the negative net charge.

In some examples, the detection circuit 1061 may detect an average value of the bidirectional pulse current signals generated by the pulse current generation circuit 200. Specifically, the net charge amounts between the negative charge amount and the positive charge amount of the bidirectional pulse current signals is directly computed, and the net charge amounts are averaged, thereby obtaining that whether a net charge exists in the total charge amount of the bidirectional pulse current signals generated by the pulse current generation circuit 200. Then, the determination circuit 1062 may determine whether an absolute value of the average value is greater than a preset value; and when the absolute value of the average value is greater than the preset value, the compensation circuit 1063 may generate a compensation pulse current signal with a net charge amount, so that the total charge amount for neural stimulation is within the safe charge amount range.

In the present embodiment, the average value of the bidirectional pulse current signals may be a current average value, an average charge value, etc. of the bidirectional pulse current signals. In addition, the preset value may be a preset current value, a preset charge value, etc.

In some examples, the average value of the bidirectional pulse current signals may be the current average value of the bidirectional pulse current signals. In this case, the detection circuit 1061 may detect the current average value of the bidirectional pulse current signals, $Ia=|(I1 \times t1+I2 \times t2)/(t1+t2)|$, wherein I2 is a negative value. The preset current value is set as I' (I'>0), and the determination circuit 1062 may determine whether Ia is greater than I'. If Ia is greater than I', then the compensation circuit 1063 generates a compensation pulse current signal with a net charge amount so that the total charge amount for neural stimulation is within the safe charge amount range. If Ia is less than or equal to I', then the compensation circuit 1063 does not work.

In some examples, the average value of the bidirectional pulse current signals may be the average charge value of the bidirectional pulse current signals. In this case, the detection circuit 1061 may detect the average charge value of the bidirectional pulse current signals, $Qa=|(I1 \times t1+I2 \times t2)/2|$, wherein I2 is a negative value. The preset charge value is set as Q' (Q'>0), and the determination circuit 1062 may determine whether Qa is greater than Q'. If Qa is greater than Q', then the compensation circuit 1063 generates a compensation pulse current signal with a net charge amount so that the total charge amount for neural stimulation is within the safe charge amount range. If Qa is less than or equal to Q', then the compensation circuit 1063 does not work.

In some examples, the detection circuit 1061 may detect the current average value of the bidirectional pulse current signals generated by the pulse current generation circuit 200, and converts the current average value into a voltage average value. In this case, the determination circuit 1062 may determine whether the absolute value of the voltage average value is greater than the preset voltage value. In this case, when the absolute value of the voltage average value is greater than the preset voltage value, the compensation circuit 1063 may generate a compensation pulse current signal with a net charge amount so that the total charge amount for neural stimulation is within the safe charge amount range.

For example, the current average value is converted into the voltage average value through a current and voltage conversion circuit, and the preset voltage value is set as a safe voltage value. When the voltage average value is lower than the preset voltage value, it indicates that the bidirectional pulse current signals generated by the pulse current generation circuit 200 have no damage to human ganglion cells or bipolar cells (without exceeding the safe charge amount range), and the compensation circuit 1063 does not need to conduct charge compensation. When the voltage average value is higher than the preset voltage value, it indicates that the bidirectional pulse current signals generated by the pulse current generation circuit 200 may have damage to human ganglion cells or bipolar cells and the compensation circuit 1063 generates a compensation pulse current signal with a net charge amount so that the total charge amount for neural stimulation is within the safe charge amount range.

In the present embodiment, the detection circuit 1061 converts the detected average current value into the voltage average value which is easily determined by the determination circuit 1062 (for example, the determination circuit 1062 may determine using a voltage comparator); it is convenient for the determination circuit 1062 to determine whether the compensation circuit 1063 needs charge compensation; and the accuracy of the outcome of the determination circuit 1062 can be enhanced.

In addition, in some examples, when the absolute value of the voltage average value is greater than the preset voltage value and the voltage average value is a positive value, the compensation circuit 1063 may generate a compensation pulse current signal with a negative net charge amount so that the total charge amount for neural stimulation is within the safe charge amount range; and when the absolute value of the voltage average value is greater than the preset voltage value and the voltage average value is a negative value, the compensation circuit 1063 generates a compensation pulse current signal with a positive net charge amount so that the total charge amount for neural stimulation is within the safe charge amount range.

In the present embodiment, the detection circuit 1061 may detect a current average value of the bidirectional pulse current signals generated by the pulse current generation circuit 200, and converts the current average value into a voltage average value. The determination circuit 1062 may determine whether an absolute value of the voltage average value is greater than a preset voltage value. When the absolute value of the voltage average value is greater than the preset voltage value and the voltage average value is a positive value, the compensation circuit 1063 generates a compensation pulse current signal with a negative net charge amount, so that the total charge amount is within the safe charge amount range. When the absolute value of the voltage average value is greater than the preset voltage value and the voltage average value is a negative value, the compensation circuit 1063 generates a compensation pulse current signal with a positive net charge amount, so that the total charge amount for neural stimulation is within the safe charge amount range.

For example, if the preset voltage value is 5 millivolt (mv), when the voltage average value is greater than 5 mv (i.e., the absolute value of the voltage average value is greater than the preset voltage value and the voltage average value is a positive value), the compensation circuit 1063 generates a compensation pulse current signal with a negative net charge amount, so that the total charge amount for neural stimulation is within the safe charge amount range. For example, the compensation pulse current signal generated by the compensation circuit 1063 is a negative pulse. In addition, when the voltage average value is less than −5 mv (i.e., the absolute value of the voltage average value is greater than the preset voltage value and the voltage average value is a negative value), the compensation circuit 1063 generates a compensation pulse current signal with a positive net charge amount, so that the total charge amount for neural stimulation is within the safe charge amount range. For example, the compensation pulse current signal generated by the compensation circuit 1063 is a positive pulse.

FIG. 11 is a schematic diagram showing a circuit structure of a charge compensation circuit according to the embodiment of the present invention. As shown in FIG. 11, the charge compensation circuit 106 may include a detection circuit 1061, a determination circuit 1062 and a compensation circuit 1063. In the present embodiment, the detection circuit 1061 may specifically include a first resistor R1, a second resistor R2 and a capacitor C1, wherein a negative pole of the first capacitor and a first end of the first resistor R1 are connected to a common voltage VSS; a positive pole of the first capacitor and a second end of the first resistor R1 are electrically connected to a second end of the second resistor R2; and a first end of the second resistor R2 is electrically connected to the pulse current generation circuit 200 and the compensation circuit 1063.

In addition, the determination circuit 1062 may specifically include a first voltage comparator U1 and a second voltage comparator U2, wherein an in-phase input end of the first voltage comparator U1 and an in-phase input end of the second voltage comparator U2 are electrically connected to the first end of the second resistor R2; a reverse-phase input end of the first voltage comparator U1 is connected to a preset positive voltage VTH+; a reverse-phase input end of the second voltage comparator U2 is connected to a preset negative voltage VTH−; a power supply end of the first voltage comparator U1 and a power supply end of the second comparator U2 are connected to a power voltage VDD; a grounding end of the first voltage comparator U1 and a grounding end of the second comparator U2 are connected to the common voltage VSS; an output end Out1 of the first voltage comparator U1 is electrically connected to a first control end C+ of the compensation circuit 1063; an output end Out2 of the second voltage comparator U2 is electrically connected to a second control end C− of the compensation circuit 1063; a power supply end of the compensation circuit 1063 is connected to the power voltage VDD; a grounding end of the compensation circuit 1063 is connected to the common voltage VSS; an output end of the compensation circuit 1063 is connected to the input end of the pulse current generation circuit 200; a power supply end of the pulse current generation circuit 200 is connected to the power voltage VDD; a grounding end of the pulse current generation circuit 200 is connected to the common voltage VSS; and an output end of the pulse current generation circuit 200 is connected to the impedance load 110.

In addition, the detection circuit 1061 may detect a total charge amount in one stimulation period T and a current average value in one stimulation period T for the bidirectional pulse current signals generated by the pulse current generation circuit 200, and converts the current average value in one stimulation period T into a voltage average value. The determination circuit 1062 may determine whether the voltage average value mentioned above is between the preset positive voltage VTH+ and the preset negative voltage VTH−. If the above voltage average value is between the preset positive voltage VTH+ and the preset negative voltage VTH−, then the compensation circuit 1063 does not need to conduct charge compensation. If the voltage average value mentioned above is not between the preset positive voltage VTH+ and the preset negative voltage VTH−, then the compensation circuit 1063 conducts charge compensation to generate a compensation pulse current signal with a net charge amount, so that the total charge amount for neural stimulation is within the safe charge amount range.

In the present embodiment, the detection circuit 1061 may be configured to detect a total charge amount in one stimulation period T for the bidirectional pulse current signals generated by the current generator 104. In some examples, the detection circuit 1061 may be formed by an integral circuit. The integral circuit may integrate the charge of the bidirectional pulse current signals generated by the current generator 104 within one stimulation period T, thereby obtaining the total charge amount of the bidirectional pulse current signals in one stimulation period T.

As a specific example, if the absolute value of the total charge amount of the bidirectional pulse current signals generated by the pulse current generation circuit 200 in one stimulation period T (e.g., the period is one second) exceeds $5 \times 10^{-7}$ coulombs, then the compensation circuit 1063 conducts charge compensation, i.e., when the current average value of the bidirectional pulse current signals is greater than $5 \times 10^{-7}$ mA or less than $-5 \times 10^{-7}$ mA, then the compensation circuit 1063 conducts charge compensation. If a resistance value of the second resistor R2 is 10 kΩ, the preset positive voltage VTH+ may be 5 mv and the preset negative voltage VTH− may be −5 mv. When the determination circuit 1062 determines that the voltage average value mentioned above exceeds 5 mv, the output end Out1 of the first voltage comparator U1 outputs a high level and the output end Out2 of the second voltage comparator U2 outputs a high level. When the determination circuit 1062 determines that the voltage average value mentioned above is lower than −5 mv, the output end Out1 of the first voltage comparator U1 outputs a low level and the output end Out2 of the second voltage comparator U2 outputs a low level. When the determination circuit 1062 determines that the voltage average value mentioned above is between −5 mv and 5 mv, the output end Out1 of the first voltage comparator U1 outputs a low level and the output end Out2 of the second voltage comparator U2 outputs a high level.

In the present embodiment, the compensation pulse current signal outputted by the output end of the compensation circuit 1063 is related to the first control end C+ of the compensation circuit 1063 and the second control end C− of the compensation circuit 1063. See Table 1 below.

TABLE 1

| First control end C+ | Second control end C− | Compensation pulse current signal |
|---|---|---|
| High level | High level | Negative pulse |
| Low level | Low level | Positive pulse |
| Low level | High level | None |

When the determination circuit 1062 determines that the above voltage average value exceeds 5 mv, the compensation circuit 1063 needs to compensate a negative pulse. At this moment, the output end Out1 of the first voltage comparator U1 outputs a high level and the output end Out2 of the second voltage comparator U2 outputs a high level, i.e., the first control end C+ is a high level and the second control end C− is a high level, as shown in Table 1. The compensation pulse current signal generated by the compensation circuit 1063 is a negative pulse.

In addition, when the determination circuit 1062 determines that the voltage average value mentioned above is lower than −5 mv, the compensation circuit 1063 needs to compensate a positive pulse. At this moment, the output end Out1 of the first voltage comparator U1 outputs a low level and the output end Out2 of the second voltage comparator U2 outputs a low level, i.e., the first control end C+ is a low level and the second control end C− is a low level, as shown in Table 1. The compensation pulse current signal generated by the compensation circuit 1063 is a positive pulse.

In addition, when the determination circuit 1062 determines that the voltage average value mentioned above is between −5 mv and 5 mv, the compensation circuit 1063 does not need to conduct charge compensation. The output end Out1 of the first voltage comparator U1 outputs a low level and the output end Out2 of the second voltage comparator U2 outputs a high level, i.e., the first control end C+ is a low level and the second control end C− is a high level, as shown in Table 1. The compensation circuit 1063 does not conduct charge compensation.

In the present embodiment, FIG. 11 only shows a specific charge compensation circuit according to a preferred embodiment of the present invention. The present embodiment is not limited to this. In the charge compensation circuit 106, the implementation of the detection circuit 1061, the determination circuit 1062 and the compensation circuit 1063 may be varied in different forms.

In addition, the charge compensation method according to in the present embodiment is a charge compensation method for conducting charge compensation on the pulse current generation circuit 200. The pulse current generation circuit 200 generates bidirectional pulse currents for neural stimulation. The charge compensation method includes: detecting the total charge amount during one stimulation period of the bidirectional pulse current signals generated by the pulse current generation circuit 200; determining whether the total charge amount detected by the detection circuit 1061 is less than or equal to the safe charge amount; and generating a compensation pulse current signal with a net charge amount when the determination circuit 1062 determines that the total charge amount exceeds the safe charge amount range, so that the total charge amount is within the safe charge amount range.

In addition, in the charge compensation method, when the determination circuit determines that the total charge amount is a positive value, a compensation pulse current signal with a negative compensation charge amount is generated so that the total charge amount is within the safe charge amount range; and when the determination circuit determines that the total charge amount is a negative value, a compensation pulse current signal with a positive compensation charge amount is generated so that the total charge amount is within the safe charge amount range. Thus, the total charge amount for neural stimulation is more effectively ensured to be within the safe charge amount range.

In some examples, when the determination circuit 1062 determines that the total charge amount of the bidirectional pulse current signals within one stimulation period T is positive, the compensation circuit 1063 conducts negative charge compensation on the bidirectional pulse current signals generated by the current generator 104. When the determination circuit 1062 determines that the total charge amount of the bidirectional pulse current signals within one stimulation period T is negative, the compensation circuit 1063 may generate a positive current pulse to conduct positive charge compensation on the bidirectional pulse current signals generated by the current generator 104. In the above charge compensation process, the compensation circuit 1063 preferably adopts a successive approximation charge compensation method, so as to gradually conduct charge compensation and enhance the accuracy of charge compensation. For example, the compensation circuit 1063 may generate a small current pulse to repeatedly conduct charge compensation on the bidirectional pulse current signals generated by the current generator 104. Herein, the net charge amount of the small current pulse generated by the compensation circuit 1063 may be positive or negative.

In addition, in one preferred embodiment, a charge convergence compensation method may be used to conduct charge compensation step by step, so as to improve the accuracy of charge compensation. In some examples, the detection circuit 1061 may detect the total charge amount of the bidirectional pulse current signals generated by the pulse current generation circuit 200 within one stimulation period T. The determination circuit 1062 may determine whether the absolute value of the total charge amount of the bidirectional pulse current signals in one stimulation period T is greater than the safe charge amount. When the determination circuit 1062 determines that the absolute value of the total charge amount of the bidirectional pulse current signals in one stimulation period T is greater than the safe charge amount, the compensation circuit 1063 conducts partial charge compensation. For example, when the determination circuit 1062 determines that the total charge amount of the bidirectional pulse current signals in one stimulation period T is Q1 and the absolute value of Q1 is greater than Qs (Qs is the safe charge amount), the compensation circuit 1063 conducts partial charge compensation. Herein, the partial charge compensation may be proportional charge compensation. For example, charge compensation is conducted according to proportion values such as 30%, 40%, 50%, 60%, 70% and 80%.

For example, assuming that the safe charge amount is $5 \times 10^{-8}$ coulombs, when the determination circuit 1062 determines that the total charge amount of the bidirectional pulse current signals in one stimulation period T is negative charge of $1 \times 10^{-7}$ coulombs, the compensation circuit 1063 may conduct positive charge compensation according to a proportion of 50%, i.e., the compensation circuit 1063 may conduct positive charge compensation of $5 \times 10^{-8}$ coulombs. Then, the detection circuit 1061 may continue to detect the total accumulated charge amount generated by the pulse current generation circuit 200. If the determination circuit 1062 determines that the total accumulated charge amount generated by the pulse current generation circuit 200 is negative charge of 6×10−8 coulombs, the compensation circuit 1063 conducts positive charge compensation of 3×10−8 coulombs. Next, the detection circuit 1061 continues to detect the total accumulated charge amount generated by the pulse current generation circuit 200. When the determination circuit 1062 determines that the total accumulated charge amount generated by the pulse current generation circuit 200 exceeds the safe charge amount range (5×10−8), the compensation circuit 1063 continues to conduct charge compensation according to a proportion of 50%; and the compensation circuit 1063 stops charge compensation until the determination circuit 1062 determines that the absolute value of the total accumulated charge amount generated by the pulse current generation circuit 200 is within the safe charge amount range. Of course, after the compensation circuit 1063 stops charge compensation, the detection circuit 1061 may continue to detect the total accumulated charge amount generated by the pulse current generation circuit 200, i.e., the detection circuit 1061 may be always in a working state to detect in real time. Once it is detected that the charge amount exceeds the standard (the absolute value of the total accumulated charge amount generated by the pulse current generation circuit 200 is greater than the safe charge amount), the compensation circuit 1063 may conduct charge compensation.

In some examples, the detection circuit 1061 may detect the total charge amount of the bidirectional pulse current signals generated by the pulse current generation circuit 200 within one stimulation period T. The determination circuit 1062 may determine whether the total charge amount of the bidirectional pulse current signals in one stimulation period T is greater than the safe charge amount. When the determination circuit 1062 determines that the total charge amount of the bidirectional pulse current signals in one stimulation period T is greater than the safe charge amount, the compensation circuit 1063 conducts partial charge compensation. For example, when the determination circuit 1062 determines that the total charge amount of the bidirectional pulse current signals in one stimulation period T is Q1 and Q1 is greater than the safe charge amount, the compensation circuit 1063 conducts partial charge compensation. Herein, the partial charge compensation may be proportional charge compensation. For example, charge compensation is conducted according to proportion values such as 30%, 40%, 50%, 60%, 70% and 80%.

For example, when the determination circuit 1062 determines that the total charge amount of the bidirectional pulse current signals in one stimulation period T is positive charge of 1×10−7 coulombs, the compensation circuit 1063 may conduct positive charge compensation according to a proportion of 50%, i.e., the compensation circuit 1063 may conduct negative charge compensation of 5×10−8 coulombs. Then, the detection circuit 1061 may continue to detect the total accumulated charge amount generated by the pulse current generation circuit 200. If the determination circuit 1062 determines that the total accumulated charge amount generated by the pulse current generation circuit 200 is positive charge of 6×10−8 coulombs, the compensation circuit 1063 may continue to conduct negative charge compensation of 3×10−8 coulombs. Next, the detection circuit 1061 may continue to detect the total accumulated charge amount generated by the pulse current generation circuit 200. When the determination circuit 1062 determines that the total accumulated charge amount generated by the pulse current generation circuit 200 exceeds the safe charge amount range, the compensation circuit 1063 may continue to conduct charge compensation according to a proportion of 50%; and the compensation circuit 1063 may stop conducting charge compensation on the pulse current generation circuit 200 until the determination circuit 1062 determines that the total accumulated charge amount generated by the pulse current generation circuit 200 is within the safe charge amount range. Of course, after the compensation circuit 1063 stops charge compensation, the detection circuit 1061 may continue to detect the total accumulated charge amount generated by the pulse current generation circuit 200, i.e., the detection circuit 1061 may be always in a working state to detect in real time. Once it is detected that the charge amount exceeds the safe charge amount range, the compensation circuit 1063 may conduct charge compensation.

While the present invention has been described in detail with reference to the drawings and embodiments, it is understood that the description mentioned above does not limit the present invention in any form. The present invention may be modified and changed as needed by those skilled in the art without departing from the spirit and scope of the present invention, and such modifications and variations are within the scope of the present invention.

What is claimed is:

1. A pulse current generation circuit for neural stimulation, comprising:
    an analogue signal receiving device for receiving an analogue signal;
    an analogue-to-digital converter for converting the analogue signal into a digital control signal;
    a current signal controller for producing, according to the digital control signal, pulse current parameters for generating bidirectional pulse current signals;
    a current generator for generating, according to the pulse current parameters, bidirectional pulse current signals for neural stimulation, wherein the current generator generates pulse currents of different precisions according to the pulse current parameters; and
    a charge compensation circuit configured to determine whether to conduct charge compensation on the current generator according to a total charge amount during one stimulation period of the bidirectional pulse current signals, so as to ensure that the total charge amount generated by the current generator is within a safe charge amount range, wherein the charge compensation circuit comprises:
    a detection circuit for detecting the total charge amount during one stimulation period of the bidirectional pulse current signals generated by the current generator,
    a determination circuit for determining whether the total charge amount detected by the detection circuit exceeds the safe charge amount range, and
    a compensation circuit for generating a compensation pulse current signal with a net charge amount when the determination circuit determines that the total charge amount exceeds the safe charge amount range, so that the total charge amount is within the safe charge amount range.

2. The pulse current generation circuit according to claim 1, wherein
    the total charge amount of the bidirectional pulse current signals is within a safe charge amount range during one stimulation period.

3. The pulse current generation circuit according to claim 1, wherein
    the pulse current parameters comprise a negative pulse width, a negative pulse amplitude, a positive pulse width, a positive pulse amplitude and a pulse interval.

4. The pulse current generation circuit according to claim 3, wherein
the current generator generates a low-precision pulse current or a high-precision pulse current according to the pulse current parameters; and
the current generator determines whether bidirectional pulse current signals to be generated are less than a critical value after receiving the pulse current parameters, generates the high-precision pulse current when the bidirectional pulse current signals to be generated are less than or equal to the critical value, and generates the low-precision pulse current when the bidirectional pulse current signals to be generated are greater than the critical value.

5. The pulse current generation circuit according to claim 4, wherein
the current generator generates the high-precision pulse current when the negative pulse width of the bidirectional pulse current signals is greater than a preset duration and the negative pulse amplitude is less than or equal to the critical value.

6. The pulse current generation circuit according to claim 4, wherein
the precision of a pulse amplitude of the high-precision pulse current is greater than the precision of a pulse amplitude of the low-precision pulse current.

7. The pulse current generation circuit according to claim 1, wherein
a total charge amount of a positive pulse current or a negative pulse current during one stimulation period of the bidirectional pulse current signals is within the safe charge amount range.

8. The pulse current generation circuit according to claim 1, wherein
in the compensation circuit, when the determination circuit determines that the total charge amount is a positive value, a first compensation pulse current signal with a negative compensation charge amount is generated so that the total charge amount is within the safe charge amount range; and
when the determination circuit determines that the total charge amount is a negative value, a second compensation pulse current signal with a positive compensation charge amount is generated so that the total charge amount is within the safe charge amount range.

9. The pulse current generation circuit according to claim 1, wherein
the amplitude of the compensation pulse current signal is lower than a preset amplitude, and a period of the compensation pulse current signal is less than a period of the bidirectional pulse current signals.

10. The pulse current generation circuit according to claim 9, wherein
the preset amplitude is a minimum current amplitude which is capable of playing a stimulation effect on the nerve tissue.

11. The pulse current generation circuit according to claim 1, wherein
in the bidirectional pulse current signals, a waveform of a positive pulse current signal is opposite to a waveform of a negative pulse current signal;
the detection circuit detects the charge amount of the positive pulse current signal and an absolute value of the charge amount of the negative pulse current signal; and
the determination circuit compares the charge amount of the positive pulse current signal with the absolute value of the charge amount of the negative pulse current signal to determine whether the total charge amount exceeds the safe charge amount range.

12. The pulse current generation circuit according to claim 1, wherein
the detection circuit detects an average value of the bidirectional pulse current signals generated by the current generator;
the determination circuit determines whether an absolute value of the average value is greater than a preset value; and
when the absolute value of the average value is greater than the preset value, the compensation circuit generates the compensation pulse current signal with a net charge amount, so that the total charge amount is within the safe charge amount range.

13. The pulse current generation circuit according to claim 1, wherein
the detection circuit detects a current average value of the bidirectional pulse current signals generated by the current generator, and converts the current average value into a voltage average value;
the determination circuit determines whether an absolute value of the voltage average value is greater than a preset voltage value; and
when the absolute value of the voltage average value is greater than the preset voltage value, the compensation circuit generates the compensation pulse current signal with a net charge amount, so that the total charge amount is within the safe charge amount range.

14. The pulse current generation circuit according to claim 10, wherein
when an absolute value of a voltage average value is greater than a preset voltage value and the voltage average value is a positive value, the compensation circuit generates a first compensation pulse current signal with a negative net charge amount so that the total charge amount for neural stimulation is within the safe charge amount range; and
when the absolute value of the voltage average value is greater than the preset voltage value and the voltage average value is a negative value, the compensation circuit generates a second compensation pulse current signal with a positive net charge amount so that the total charge amount for neural stimulation is within the safe charge amount range.

15. The pulse current generation circuit according to claim 1, wherein
the compensation circuit adopts a charge compensation method by successive approximation.

16. An implantable electrical retina stimulator, comprising:
an implanted device comprising the pulse current generation circuit according to claim 1;
a video recording device configured to capture a video image and convert the video image into a visual signal;
a video processing device connected with the video recording device and configured to process the visual signal to generate a modulation signal; and
an analogue signal transmitting device configured to transmit the modulation signal to the implanted device,
wherein the implanted device converts the received modulation signal into the bidirectional pulse current signals used as electrical stimulation signals, so as to transmit the bidirectional pulse current signals for ganglion cells or bipolar cells of the retina to generate a sense of light.

17. The implantable electrical retina stimulator according to claim 16, wherein a total charge amount of the bidirectional pulse current signals is within a safe charge amount range during one stimulation period.

18. The implantable electrical retina stimulator according to claim 16, wherein the pulse current parameters comprise a negative pulse width, a negative pulse amplitude, a positive pulse width, a positive pulse amplitude and a pulse interval.

19. The implantable electrical retina stimulator according to claim 16, wherein a total charge amount of a positive pulse current or a negative pulse current during one stimulation period of the bidirectional pulse current signals is within a safe charge amount range.

* * * * *